US011339397B2

(12) United States Patent
Bai et al.

(10) Patent No.: US 11,339,397 B2
(45) Date of Patent: May 24, 2022

(54) **EXPRESSION OF PHYTASE IN *ASPERGILLUS NIGER***

(71) Applicant: Nanjing Bestzyme Bio-Engineering Co., Ltd., Jiangsu (CN)

(72) Inventors: Aixi Bai, Jiangsu (CN); Feng Li, Jiangsu (CN); Furong Bian, Jiangsu (CN); Jidong Zhu, Jiangsu (CN); Yan Sun, Jiangsu (CN); Hong Xu, Jiangsu (CN)

(73) Assignee: Nanjing Bestzyme Bio-Engineering Co., Ltd., Jiangsu (CN)

( * ) Notice: Subject to any disclaimer, the term of this patent is extended or adjusted under 35 U.S.C. 154(b) by 0 days.

(21) Appl. No.: 16/498,570

(22) PCT Filed: Mar. 30, 2018

(86) PCT No.: PCT/CN2018/081272
§ 371 (c)(1),
(2) Date: Sep. 27, 2019

(87) PCT Pub. No.: WO2018/177402
PCT Pub. Date: Oct. 4, 2018

(65) Prior Publication Data
US 2021/0032637 A1 Feb. 4, 2021

(30) Foreign Application Priority Data

Mar. 30, 2017 (CN) .......................... 201710203473.5
Aug. 25, 2017 (CN) .......................... 201710741963.0

(51) Int. Cl.
*C12N 15/67* (2006.01)
*C12N 9/16* (2006.01)
*C12N 15/80* (2006.01)

(52) U.S. Cl.
CPC .............. *C12N 15/67* (2013.01); *C12N 9/16* (2013.01); *C12N 15/80* (2013.01); *C07K 2319/02* (2013.01); *C12N 2800/22* (2013.01); *C12Y 301/03* (2013.01)

(58) Field of Classification Search
None
See application file for complete search history.

(56) References Cited

U.S. PATENT DOCUMENTS

| 5,536,661 | A | * | 7/1996 | Boel .................. A01H 5/02 435/198 |
| 7,135,323 | B2 | * | 11/2006 | Lanahan ............... A23K 40/25 435/196 |
| 2005/0026268 | A1 | | 2/2005 | Apajalahti et al. |
| 2012/0021488 | A1 | | 1/2012 | Ye et al. |
| 2012/0041171 | A1 | | 2/2012 | Van Peij et al. |

FOREIGN PATENT DOCUMENTS

| CN | 102414323 A | 4/2012 |
| EP | 0238023 A2 | 9/1987 |
| WO | 0136607 A1 | 5/2001 |
| WO | 03057247 A1 | 7/2003 |
| WO | 03057248 A1 | 7/2003 |
| WO | 03070957 A2 | 8/2003 |
| WO | 2006077258 A1 | 7/2006 |
| WO | 2008000632 A1 | 1/2008 |
| WO | 2010121933 A1 | 10/2010 |

OTHER PUBLICATIONS

International Search Report of International Application No. PCT/CN2018/081272 dated Jul. 9, 2018, English translation.
Nielsen et al., "Performance of Microbial Phytases for Gastric Inositol Phosphate Degradation," J Agric Food Chem, vol. 63, No. 3, pp. 943-950 (2015).
Extended European Search Report for App. No. EP18774340.6 dated Dec. 11, 2020, 13 pages.
Rodriguez E. et al.: "Cloning, sequencing, and expression of an *Escherichia coli* acid phosphatase/phytase gene (appA2) isolated from pig colon", Biochemical and Biophysical Research Communications, vol. 257, No. 1, Apr. 2, 1999 (Apr. 2, 1999) pp. 117-123.

* cited by examiner

*Primary Examiner* — Suzanne M Noakes
(74) *Attorney, Agent, or Firm* — Ice Miller LLP

(57) ABSTRACT

Disclosed herein is a method for expressing phytase in a filamentous fungus by using an optimized *Escherichia coli* phytase gene having a nucleotide sequence as shown in SEQ ID NO. 7 and a signal peptide having a nucleotide sequence as shown in SEQ ID NO. 12.

6 Claims, 5 Drawing Sheets

Specification includes a Sequence Listing.

FIGURES

SEQUENCE LISTING

<160> NUMBER OF SEQ ID NOS: 48

<210> SEQ ID NO 1
<211> LENGTH: 1329
<212> TYPE: DNA
<213> ORGANISM: Artificial Sequence
<220> FEATURE:
<223> OTHER INFORMATION: DNA sequence encoding Escherichia coli phytase

<400> SEQUENCE: 1

```
atgtcagata tgaaaagcgg aaacatatcg atgaaagcga tcttaatccc attttatct      60 cttctgattc cgttaacccc gcaatctgca ttcgctcaga gtgagccgga gctgaagctg     120
gaaagtgtgg tgattgtcag tcgtcatggt gtgcgtgctc caaccaaggc cacgcaactg     180
atgcaggatg tcaccccaga cgcatggcca acctggccga taaaactggg ttggctgaca     240
ccgcgcggtg gtgagctaat cgcctatctc ggacattacc aacgccagcg tctggtagcc     300
gacggattgc tggcgaaaaa gggctgcccg cagtctggtc aggtcgcgat tattgctgat     360
gtcgacgagc gtacccgtaa aacaggcgaa gccttcgccg ccgggctggc acctgactgt     420
gcaataaccg tacatacccca ggcagatacg tccagtcccg atccgttatt taatcctcta     480
aaaactggcg tttgccaact ggataactcg aacgtgactg acgcgatcct cagcagggca     540
ggagggtcaa ttgctgactt taccgggcat cggcaaacgg cgtttcgcga actggaacgg     600
gtgcttaatt ttccgcaatc aaacttgtgc cttaaacgtg agaaacagga cgaaagctgt     660
tcattaacgc aggcattacc atcggaactc aaggtgagcg ccgacaatgt ctcattaacc     720
ggtgcggtaa gcctcgcatc aatgctgacg gagatatttc tcctgcaaca agcacaggga     780
atgccggagc cgggtgggg aaggatcacc gattcacacc agtggaacac cttgctaagt     840
ttgcataacg cgcaatttta tttgctacaa cgcacgccag aggttgcccg cagccgcgcc     900
accccgttat tagatttgat caagacagcg ttgacgcccc atccaccgca aaaacaggcg     960
tatggtgtga cattacccac ttcagtgctg tttatcgccg gacacgatac taatctggca    1020
aatctcggcg gcgcactgga gctcaactgg acgcttcccg gtcagccgga taacacgccg    1080
ccaggtggtg aactggtgtt tgaacgctgg cgtcggctaa gcgataacag ccagtggatt    1140
```

-continued

```
caggtttcgc tggtcttcca gactttacag cagatgcgtg ataaaacgcc gctgtcatta   1200
aatacgccgc ccggagaggt gaaactgacc ctggcaggat gtgaagagcg aaatgcgcag   1260
ggcatgtgtt cgttggcagg ttttacgcaa atcgtgaatg aagcacgcat accggcgtgc   1320
agtttgtaa                                                            1329
```

<210> SEQ ID NO 2
<211> LENGTH: 442
<212> TYPE: PRT
<213> ORGANISM: Artificial Sequence
<220> FEATURE:
<223> OTHER INFORMATION: Amino acid sequence of Escherichia coli phytase

<400> SEQUENCE: 2

```
Met Ser Asp Met Lys Ser Gly Asn Ile Ser Met Lys Ala Ile Leu Ile
1               5                   10                  15

Pro Phe Leu Ser Leu Leu Ile Pro Leu Thr Pro Gln Ser Ala Phe Ala
            20                  25                  30

Gln Ser Glu Pro Glu Leu Lys Leu Glu Ser Val Val Ile Val Ser Arg
        35                  40                  45

His Gly Val Arg Ala Pro Thr Lys Ala Thr Gln Leu Met Gln Asp Val
    50                  55                  60

Thr Pro Asp Ala Trp Pro Thr Trp Pro Val Lys Leu Gly Trp Leu Thr
65                  70                  75                  80

Pro Arg Gly Gly Glu Leu Ile Ala Tyr Leu Gly His Tyr Gln Arg Gln
                85                  90                  95

Arg Leu Val Ala Asp Gly Leu Leu Ala Lys Lys Gly Cys Pro Gln Ser
            100                 105                 110

Gly Gln Val Ala Ile Ile Ala Asp Val Asp Glu Arg Thr Arg Lys Thr
        115                 120                 125

Gly Glu Ala Phe Ala Ala Gly Leu Ala Pro Asp Cys Ala Ile Thr Val
    130                 135                 140

His Thr Gln Ala Asp Thr Ser Ser Pro Asp Pro Leu Phe Asn Pro Leu
145                 150                 155                 160

Lys Thr Gly Val Cys Gln Leu Asp Asn Ser Asn Val Thr Asp Ala Ile
                165                 170                 175

Leu Ser Arg Ala Gly Gly Ser Ile Ala Asp Phe Thr Gly His Arg Gln
            180                 185                 190

Thr Ala Phe Arg Glu Leu Glu Arg Val Leu Asn Phe Pro Gln Ser Asn
        195                 200                 205

Leu Cys Leu Lys Arg Glu Lys Gln Asp Glu Ser Cys Ser Leu Thr Gln
    210                 215                 220

Ala Leu Pro Ser Glu Leu Lys Val Ser Ala Asp Asn Val Ser Leu Thr
225                 230                 235                 240

Gly Ala Val Ser Leu Ala Ser Met Leu Thr Glu Ile Phe Leu Leu Gln
                245                 250                 255

Gln Ala Gln Gly Met Pro Glu Pro Gly Trp Gly Arg Ile Thr Asp Ser
            260                 265                 270

His Gln Trp Asn Thr Leu Leu Ser Leu His Asn Ala Gln Phe Tyr Leu
        275                 280                 285

Leu Gln Arg Thr Pro Glu Val Ala Arg Ser Arg Ala Thr Pro Leu Leu
    290                 295                 300

Asp Leu Ile Lys Thr Ala Leu Thr Pro His Pro Pro Gln Lys Gln Ala
305                 310                 315                 320

Tyr Gly Val Thr Leu Pro Thr Ser Val Leu Phe Ile Ala Gly His Asp
```

```
                    325                 330                 335
Thr Asn Leu Ala Asn Leu Gly Gly Ala Leu Glu Leu Asn Trp Thr Leu
                340                 345                 350

Pro Gly Gln Pro Asp Asn Thr Pro Pro Gly Gly Glu Leu Val Phe Glu
            355                 360                 365

Arg Trp Arg Arg Leu Ser Asp Asn Ser Gln Trp Ile Gln Val Ser Leu
        370                 375                 380

Val Phe Gln Thr Leu Gln Gln Met Arg Asp Lys Thr Pro Leu Ser Leu
385                 390                 395                 400

Asn Thr Pro Pro Gly Glu Val Lys Leu Thr Leu Ala Gly Cys Glu Glu
                405                 410                 415

Arg Asn Ala Gln Gly Met Cys Ser Leu Ala Gly Phe Thr Gln Ile Val
            420                 425                 430

Asn Glu Ala Arg Ile Pro Ala Cys Ser Leu
        435                 440

<210> SEQ ID NO 3
<211> LENGTH: 1233
<212> TYPE: DNA
<213> ORGANISM: Artificial Sequence
<220> FEATURE:
<223> OTHER INFORMATION: DNA sequence encoding Escherichia coli phytase
      mature peptide

<400> SEQUENCE: 3
cagagtgagc ggagctgaa gctggaaagt gtggtgattg tcagtcgtca tggtgtgcgt      60
gctccaacca aggccacgca actgatgcag gatgtcaccc cagacgcatg gccaacctgg     120
ccggtaaaac tgggttggct gacaccgcgc ggtggtgagc taatcgccta tctcggacat     180
taccaacgcc agcgtctggt agccgacgga ttgctggcga aaaagggctg cccgcagtct     240
ggtcaggtcg cgattattgc tgatgtcgac gagcgtaccc gtaaaacagg cgaagccttc     300
gccgccgggc tggcacctga ctgtgcaata accgtacata cccaggcaga tacgtccagt     360
cccgatccgt tatttaatcc tctaaaaact ggcgtttgcc aactggataa ctcgaacgtg     420
actgacgcga tcctcagcag ggcaggaggg tcaattgctg actttaccgg cgcatcggca     480
acggcgtttc gcgaactgga acgggtgctt aattttccgc aatcaaactt gtgccttaaa     540
cgtgagaaac aggacgaaag ctgttcatta acgcaggcat taccatcgga actcaaggtg     600
agcgccgaca atgtctcatt aaccggtgcg gtaagcctcg catcaatgct gacggagata     660
tttctcctgc aacaagcaca gggaatgccg gagccgggt ggggaaggat caccgattca     720
caccagtgga acaccttgct aagtttgcat aacgcgcaat tttatttgct acaacgcacg     780
ccagaggttg cccgcagccg cgccacccg ttattagatt tgatcaagac agcgttgacg     840
ccccatccac cgcaaaaaca ggcgtatggt gtgacattac ccacttcagt gctgtttatc     900 gccgacacg atactaatct ggcaaatctc ggcggcgcac tggagctcaa ctggacgctt     960
ccgggtcagc cggataacac gccgccaggt ggtgaactgg tgtttgaacg ctggcgtcgg    1020
ctaagcgata acagccagtg gattcaggtt cgctggtctt tccagacttt acagcagatg    1080
cgtgataaaa cgccgctgtc attaaatacg ccgccggag aggtgaaact gaccctggca    1140
ggatgtgaag agcgaaatgc gcagggcatg tgttcgttgg caggttttac gcaaatcgtg    1200
aatgaagcac gcataccggc gtgcagtttg taa                                 1233

<210> SEQ ID NO 4
<211> LENGTH: 410
```

<212> TYPE: PRT
<213> ORGANISM: Artificial Sequence
<220> FEATURE:
<223> OTHER INFORMATION: Mature peptide sequence of Escherichia coli phytase

<400> SEQUENCE: 4

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ser Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380
```

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 5
<211> LENGTH: 96
<212> TYPE: DNA
<213> ORGANISM: Artificial Sequence
<220> FEATURE:
<223> OTHER INFORMATION: DNA sequence encoding Escherichia coli phytase
      signal peptide

<400> SEQUENCE: 5
atgtcagata tgaaaagcgg aaacatatcg atgaaagcga tcttaatccc atttttatct    60
cttctgattc cgttaacccc gcaatctgca ttcgct                              96

<210> SEQ ID NO 6
<211> LENGTH: 32
<212> TYPE: PRT
<213> ORGANISM: Artificial Sequence
<220> FEATURE:
<223> OTHER INFORMATION: Escherichia coli phytase signal peptide
      sequence

<400> SEQUENCE: 6

Met Ser Asp Met Lys Ser Gly Asn Ile Ser Met Lys Ala Ile Leu Ile
1               5                   10                  15

Pro Phe Leu Ser Leu Leu Ile Pro Leu Thr Pro Gln Ser Ala Phe Ala
            20                  25                  30

<210> SEQ ID NO 7
<211> LENGTH: 1329
<212> TYPE: DNA
<213> ORGANISM: Artificial Sequence
<220> FEATURE:
<223> OTHER INFORMATION: Optimized DNA sequence encoding Escherichia
      coli phytase

<400> SEQUENCE: 7
atgtccgaca tgaagtccgg taacatctcc atgaaggcca tcctgatccc cttcctgtcc    60
ctgctgatcc ccctgacccc ccagtccgcc ttcgcccagt ccgagcccga gctcaagctc   120
gagtccgtcg tcatcgtctc ccgccacggt gtccgcgccc ccaccaaggc cacccagctc   180
atgcaggacg tcaccccccga cgcctggccc acctggcccg tcaagctcgg ttggctcacc   240 cccgcggtg gtgagctcat cgcctacctc ggtcactacc agcgccagcg cctcgtcgcc   300
gacggtctcc tcgccaagaa gggttgcccc cagtccggtc aggtcgccat catcgccgac   360
gtcgacgagc gcacccgcaa gaccggtgag gccttcgccg ccggtctcgc ccccgactgc   420
gccatcaccg tccacaccca ggccgacacc tcctcccccg acccctcctt caaccccctc   480
aagaccggtg tctgccagct cgacaactcc aacgtcaccg cgccatcct ctcccgcgcc   540 ggtggttcca tcgccgactt caccggtcac cgccagaccg ccttccgcga gctcgagcgc   600
gtcctcaact ccccccagtc caacctctgc ctcaagcgcg agaagcagga cgagtcctgc   660
tccctcaccc aggccctccc ctccgagctc aaggtctccg ccgacaacgt ctccctcacc   720
ggtgccgtct ccctcgcctc catgctcacc gagatcttcc tcctccagca ggcccagggt   780 atgccccgagc ccgttggggg tcgcatcacc gactcccacc agtggaacac cctcctctcc   840
ctccacaacg cccagttcta cctcctccag cgcaccccccg aggtcgcccg ctcccgcgcc   900

```
acccccctcc tcgacctcat caagaccgcc ctcacccccc acccccccca gaagcaggcc    960
tacggtgtca ccctccccac ctccgtcctc ttcatcgccg gtcacgacac caacctcgcc   1020
aacctcggtg gtgccctcga gctcaactgg accctccccg gtcagcccga caacacccccc  1080 cccggtggtg agctcgtctt cgagcgctgg cgccgcctct ccgacaactc ccagtggatc   1140
caggtctccc tcgtcttcca gaccctccag cagatgcgcg acaagacccc cctctcccctc  1200 aacacccccc ccggtgaggt caagctcacc ctcgccggtt gcgaggagcg caacgcccag   1260
ggtatgtgct ccctcgccgg tttcacccag atcgtcaacg aggcccgcat ccccgcctgc   1320
tccctctaa                                                            1329

<210> SEQ ID NO 8
<211> LENGTH: 1233
<212> TYPE: DNA
<213> ORGANISM: Artificial Sequence
<220> FEATURE:
<223> OTHER INFORMATION: Optimized DNA sequence encoding Escherichia
      coli phytase mature peptide

<400> SEQUENCE: 8
cagtccgagc ccgagctcaa gctcgagtcc gtcgtcatcg tctcccgcca cggtgtccgc     60
gcccccacca aggccaccca gctcatgcag gacgtcaccc ccgacgcctg gcccacctgg    120
cccgtcaagc tcggttggct caccccccgc ggtggtgagc tcatcgccta cctcggtcac    180
taccagcgcc agcgcctcgt cgccgacggt ctcctcgcca agaagggttg ccccccagtcc    240 ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgaccccc tcttcaaccc cctcaagacc ggtgtctgcc agctcgacaa ctccaacgtc    420
accgacgcca tcctctcccg cgccggtggt tccatcgccg acttcaccgg tcaccgccag    480
accgccttcc gcgagctcga gcgcgtcctc aacttcccccc agtccaacct ctgcctcaag    540
cgcgagaagc aggacgagtc ctgctccctc acccaggccc tccctccga gctcaaggtc    600 tccgccgaca cgtctccct caccggtgcc gtctccctcg cctccatgct caccgagatc    660
ttcctcctcc agcaggccca gggtatgccc gagcccggtt ggggtcgcat caccgactcc    720
caccagtgga cacccctcct ctcccctccac aacgcccagt tctacctcct ccagcgcacc    780
cccgaggtcg cccgctcccg cgccacccccc ctcctcgacc tcatcaagac cgccctcacc    840
ccccaccccc cccagaagca ggcctacggt gtcaccctcc ccacctccgt cctcttcatc    900
gccggtcacg acaccaacct cgccaacctc ggtggtgccc tcgagctcaa ctggacccctc    960 cccggtcagc ccgacaacac ccccccccggt ggtgagctcg tcttcgagcg ctggcgccgc   1020
ctctccgaca actcccagtg gatccaggtc tcccctcgtct tccagaccct ccagcagatg   1080
cgcgacaaga ccccccctctc cctcaacacc cccccggtg aggtcaagct caccctcgcc   1140
ggttgcgagg agcgcaacgc ccagggtatg tgctccctcg ccggtttcac ccagatcgtc   1200
aacgaggccc gcatccccgc ctgctccctc taa                                 1233

<210> SEQ ID NO 9
<211> LENGTH: 96
<212> TYPE: DNA
<213> ORGANISM: Artificial Sequence
<220> FEATURE:
<223> OTHER INFORMATION: Optimized DNA sequence encoding Escherichia
      coli phytase signal peptide
```

-continued

<400> SEQUENCE: 9
atgtccgaca tgaagtccgg taacatctcc atgaaggcca tcctgatccc cttcctgtcc    60
ctgctgatcc ccctgacccc ccagtccgcc ttcgcc    96

<210> SEQ ID NO 10
<211> LENGTH: 75
<212> TYPE: DNA
<213> ORGANISM: Artificial Sequence
<220> FEATURE:
<223> OTHER INFORMATION: DNA sequence encoding Aspergillus niger
      glycosylase signal peptide

<400> SEQUENCE: 10
atgtcgttcc gatctctact cgccctgagc ggcctcgtct gcacagggtt ggcaaatgtg    60
atttccaagc gcgcg    75

<210> SEQ ID NO 11
<211> LENGTH: 25
<212> TYPE: PRT
<213> ORGANISM: Artificial Sequence
<220> FEATURE:
<223> OTHER INFORMATION: Amino acid sequence of Aspergillus niger
      glycosylase signal peptide

<400> SEQUENCE: 11

Met Ser Phe Arg Ser Leu Leu Ala Leu Ser Gly Leu Val Cys Thr Gly
1               5                   10                  15

Leu Ala Asn Val Ile Ser Lys Arg Ala
            20                  25

<210> SEQ ID NO 12
<211> LENGTH: 84
<212> TYPE: DNA
<213> ORGANISM: Artificial Sequence
<220> FEATURE:
<223> OTHER INFORMATION: DNA sequence encoding Aspergillus oryzae TAKA
      amylase signal peptide

<400> SEQUENCE: 12
atggtcgcct ggtggtccct cttcctctac ggtctccagg tcgccgcccc cgccctcgcc    60 gccaccccg ccgactggcg ctcc    84

<210> SEQ ID NO 13
<211> LENGTH: 28
<212> TYPE: PRT
<213> ORGANISM: Artificial Sequence
<220> FEATURE:
<223> OTHER INFORMATION: Amino acid sequence of Aspergillus oryzae TAKA
      amylase signal peptide

<400> SEQUENCE: 13

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser
            20                  25

<210> SEQ ID NO 14
<211> LENGTH: 1233
<212> TYPE: DNA
<213> ORGANISM: Artificial Sequence
<220> FEATURE:
<223> OTHER INFORMATION: Optimized DNA sequence encoding Escherichia
      coli phytase mutant NOV9X mature peptide

<400> SEQUENCE: 14

```
cagtccgagc cgagctcaa gctcgagtcc gtcgtcatcg tctcccgcca cggtgtccgc      60
gcccccacca aggccaccca gctcatgcag gacgtcaccc ccgacgcctg gcccacctgg     120
cccgtcaagc tcggtgagct caccccccgc ggtggtgagc tcatcgccta cctcggtcac    180
tactggcgcc agcgcctcgt cgccgacggt ctcctcccca agtgcggttg cccccagtcc    240
ggtcaggtcg ccatcatcgc cgacgtcgac gagcgcaccc gcaagaccgg tgaggccttc     300
gccgccggtc tcgcccccga ctgcgccatc accgtccaca cccaggccga cacctcctcc    360
cccgaccccc tcttcaaccc cctcaagacc ggtgtctgcc agctcgacaa cgccaacgtc    420
accgacgcca tcctcgagcg cgccggtggt tccatcgccg acttcaccgg tcactaccag    480
accgccttcc gcgagctcga gcgcgtcctc aacttccccc agtccaacct ctgcctcaag    540
cgcgagaagc aggacgagtc ctgctccctc acccaggccc tcccctccga gctcaaggtc    600
tccgccgact gcgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctccctccac aacgcccagt tcgacctcct ccagcgcacc    780
cccgaggtcg cccgctcccg cgccacccccc ctcctcgacc tcatcaagac cgccctcacc    840
ccccacccccc cccagaagca ggcctacggt gtcaccctcc ccacctccgt cctcttcatc    900
gccggtcacg acaccaacct cgccaacctc ggtggtgccc tcgagctcaa ctggacccctc    960
cccggtcagc ccgacaacac ccccccccggt ggtgagctcg tcttcgagcg ctggcgccgc   1020
ctctccgaca ctcccagtg gatccaggtc tccctcgtct ccagaccct ccagcagatg    1080
cgcgacaaga ccccctctc cctcaacacc ccccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                1233
```

<210> SEQ ID NO 15
<211> LENGTH: 410
<212> TYPE: PRT
<213> ORGANISM: Artificial Sequence
<220> FEATURE:
<223> OTHER INFORMATION: Optimized Escherichia coli phytase mutant NOV9X
      mature peptide sequence

<400> SEQUENCE: 15

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125
```

```
Lys Thr Gly Val Cys Gln Leu Asp Asn Ala Asn Val Thr Asp Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Cys Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 16
<211> LENGTH: 1233
<212> TYPE: DNA
<213> ORGANISM: Artificial Sequence
<220> FEATURE:
<223> OTHER INFORMATION: Optimized DNA sequence encoding Escherichia
      coli phytase mutant NOV9XM mature peptide

<400> SEQUENCE: 16
cagtccgagc cgagctcaa gctccagtcc gtcgtcatcg tctcccgcca cggtgtccgc      60
gcccccaccc gcgccaccca gctcatgcag aacgtcaccc ccgacgcctg gcccacctgg    120
aaccagaccc tcggtgagct caccccccgc ggtggtgagc tcatcgccta cctcggtcac    180
tactggcgcc agcgcctcgt cgccgacggt ctcctcccca accagacctg ccccagtcc    240 ggtcaggtcg ccatcatcgc cgacaccgac gagcgcaccc gcaagacggt tgaggccttc    300
gccgccggtc tcgcccccga ctgcgccatc accgtccaca cccaggccga cacctcctcc    360 cccgacccc tcttcaaccc cctccgcacc ggtgtctgcc agctcgacaa cgccaacgtc    420
```

```
accgacgcca tcctcgagcg cgccggtggt tccatcgccg acttcaccgg tcactaccag    480
accgccttcc gcgagctcga gcgcgtcctc aacttctccc agtccaacct ctgcctcaag    540
cgcgagaagg aggacgagtc ctgctccctc acccaggccc tccctccga gctcaaggtc     600 tccgccgact gcgtctccct caccggtgcc gtccctcg cctccatgct caccgagatc      660
ttcctcctcc agcaggccca gggtatgccc gagcccggtt ggggtcgcat caccgactcc    720
caccagtgga cacctcct ctccctccac aacgcccagt cgacctcct caaccgcacc       780 cccgaggtcg cccgctcccg cgccaccccc ctcctcgacc tcatcaagac cgccctcacc    840
cccaacggta cccagaagca ggccaagggg gtcaccctcc ccacctccgt cctcttcatc    900
gccggtcacg acaccaacct cgccaacctc ggtggtgccc tcgagctcaa ctggacccctc  960 cccggtcagc ccgacaacac cccccccggt ggtgagctcg tcttcgagcg ctggcgccgc    1020
ctctccgaca actcccagtg gatcaacgtc tccctcgtct tccagaccct ccagcagatg    1080
cgcgacaaga cccccctctc cctcaacacc cccccggtg aggtcaagct caccctcgcc     1140
ggttgcgagg agcgcaacgc ccagggtatg tgctcccctcg ccggtttcac ccagatcgtc   1200
aacgaggccc gcctccccgc ctgctccctc taa                                 1233
```

<210> SEQ ID NO 17
<211> LENGTH: 410
<212> TYPE: PRT
<213> ORGANISM: Artificial Sequence
<220> FEATURE:
<223> OTHER INFORMATION: Optimized Escherichia coli phytase mutant
    NOV9XM mature peptide sequence

<400> SEQUENCE: 17

```
Gln Ser Glu Pro Glu Leu Lys Leu Gln Ser Val Val Ile Val Ser Arg
1               5                   10                  15

His Gly Val Arg Ala Pro Thr Arg Ala Thr Gln Leu Met Gln Asn Val
                20                  25                  30

Thr Pro Asp Ala Trp Pro Thr Trp Asn Gln Thr Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Gly Leu Leu Pro Asn Gln Thr Cys Pro Gln Ser
65                  70                  75                  80

Gly Gln Val Ala Ile Ile Ala Asp Thr Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Arg Thr Gly Val Cys Gln Leu Asp Asn Ala Asn Val Thr Asp Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Glu Asp Glu Ser Cys Ser Leu Thr Gln
            180                 185                 190

Ala Leu Pro Ser Glu Leu Lys Val Ser Ala Asp Cys Val Ser Leu Thr
        195                 200                 205

Gly Ala Val Ser Leu Ala Ser Met Leu Thr Glu Ile Phe Leu Leu Gln
```

```
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Asn Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Lys Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Asn Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Leu Pro Ala Cys Ser Leu
                405                 410

<210> SEQ ID NO 18
<211> LENGTH: 2515
<212> TYPE: DNA
<213> ORGANISM: Artificial Sequence
<220> FEATURE:
<223> OTHER INFORMATION: hph gene expression cassette

<400> SEQUENCE: 18
gtacagtgac cggtgactct ttctggcatg cggagagacg gacggacgca gagagaaggg      60
ctgagtaata agccactggc cagacagctc tggcggctct gaggtgcagt ggatgattat     120
taatccggga ccggccgccc ctccgccccg aagtggaaag gctggtgtgc ccctcgttga     180
ccaagaatct attgcatcat cggagaatat ggagcttcat cgaatcaccg gcagtaagcg     240
aaggagaatg tgaagccagg ggtgtatagc cgtcggcgaa atagcatgcc attaacctag     300
gtacagaagt ccaattgctt ccgatctggt aaaagattca cgagatagta ccttctccga     360
agtaggtaga gcgagtaccc ggcgcgtaag ctccctaatt ggcccatccg gcatctgtag     420
ggcgtccaaa tatcgtgcct ctcctgcttt gcccggtgta tgaaaccgga aaggccgctc     480
aggagctggc cagcggcgca gaccgggaac acaagctggc agtcgaccca tccggtgctc     540
tgcactcgac ctgctgaggt ccctcagtcc ctggtaggca gctttgcccc gtctgtccgc     600
ccggtgtgtc ggcggggttg acaaggtcgt tgcgtcagtc aacatttgt tgccatattt      660 tcctgctctc cccaccagct gctctttct tttctctttc ttttcccatc ttcagtatat      720
tcatcttccc atccaagaac ctttatttcc cctaagtaag tactttgcta catccatact     780
ccatccttcc catcccttat tcctttgaac ctttcagttc gagctttccc acttcatcgc     840
agcttgacta acagctaccc cgcttgagca gacatcacca tgaaaaagcc tgaactcacc     900
gcgacgtctg tcgagaagtt tctgatcgaa aagttcgaca gcgtctccga cctgatgcag     960
```

```
ctctcggagg gcgaagaatc tcgtgctttc agcttcgatg taggagggcg tggatatgtc    1020
ctgcgggtaa atagctgcgc cgatggtttc tacaaagatc gttatgttta tcggcactttt   1080 gcatcggccg cgctcccgat tccggaagtg cttgacattg gggagttcag cgagagcctg    1140
acctattgca tctcccgccg tgcacagggt gtcacgttgc aagacctgcc tgaaaccgaa    1200
ctgcccgctg ttctgcagcc ggtcgcggag gccatggatg cgatcgctgc ggccgatctt    1260
agccagacga gcgggttcgg cccattcgga ccgcaaggaa tcggtcaata cactacatgg    1320
cgtgatttca tatgcgcgat tgctgatccc catgtgtatc actggcaaac tgtgatggac    1380
gacaccgtca gtgcgtccgt cgcgcaggct ctcgatgagc tgatgctttg gccgaggac    1440 tgccccgaag tccggcacct cgtgcacgcg gatttcggct ccaacaatgt cctgacggac    1500
aatggccgca taacagcggt cattgactgg agcgaggcga tgttcgggga ttcccaatac    1560
gaggtcgcca acatcttctt ctggaggccg tggttggctt gtatggagca gcagacgcgc    1620
tacttcgagc ggaggcatcc ggagcttgca ggatcgccgc ggctccgggc gtatatgctc    1680
cgcattggtc ttgaccaact ctatcagagc ttggttgacg caatttcga tgatgcagct    1740 tgggcgcagg gtcgatgcga cgcaatcgtc cgatccggag ccgggactgt cgggcgtaca    1800
caaatcgccc gcagaagcgc ggccgtctgg accgatggct gtgtagaagt actcgccgat    1860
agtggaaacc gacgcccag cactcgtccg agggcaaagg aatagtgatt taatagctcc     1920
atgtcaacaa gaataaaacg cgttttcggg tttacctctt ccagatacag ctcatctgca    1980
atgcattaat gcattgactg caacctagta acgccttcag gctccggcga agagaagaat    2040
agcttagcag agctattttc attttcggga gacgagatca agcagatcaa cggtcgtcaa    2100
gagacctacg agactgagga atccgctctt ggctccacgc gactatatat ttgtctctaa    2160
ttgtactttg acatgctcct cttctttact ctgatagctt gactatgaaa attccgtcac    2220
cagccctggg ttcgcaaaga taattgcatg tttcttcctt gaactctcaa gcctacagga    2280
cacacattca tcgtaggtat aaacctcgaa atcattccta ctaagatggt atacaatagt    2340
aaccatggtt gcctagtgaa tgctccgtaa cacccaatac gccggccgaa actttttac    2400 aactctccta tgagtcgttt acccagaatg cacaggtaca cttgtttaga ggtaatcctt    2460
ctttctagaa gtcctcgtgt actgtgtaag cgcccactcc acatctccac tcgag         2515
```

<210> SEQ ID NO 19
<211> LENGTH: 1979
<212> TYPE: DNA
<213> ORGANISM: Artificial Sequence
<220> FEATURE:
<223> OTHER INFORMATION: HSV-tk expression cassette

<400> SEQUENCE: 19

```
ggatcccggg tctacgccag gaccgagcaa gcccagatga gaaccgacgc agatttcctt     60
ggcacctgtt gcttcagctg aatcctggca atacgagata cctgctttga atattttgaa    120
tagctcgccc gctggagagc atcctgaatg caagtaacaa ccgtagaggc tgacacggca    180
ggtgttgcta gggagcgtcg tgttctacaa ggccagacgt cttcgcggtt gatatatatg    240
tatgtttgac tgcaggctgc tcagcgacga cagtcaagtt cgccctcgct gcttgtgcaa    300
taatcgcagt ggggaagcca caccgtgact cccatctttc agtaaagctc tgttggtgtt    360
tatcagcaat acacgtaatt taaactcgtt agcatgggc tgatagctta attaccgttt     420
accagtgccg cggttctgca gctttccttg gcccgtaaaa ttcggcgaag ccagccaatc    480
```

```
accagctagg caccagctaa accctataat tagtctctta tcaacaccat ccgctccccc      540
gggatcaatg aggagaatga gggggatgcg gggctaaaga agcctacata accctcatgc      600
caactcccag tttacactcg tcgagccaac atcctgacta taagctaaca cagaatggct      660
tcgtacccct gccatcaaca cgcgtctgcg ttcgaccagg ctgcgcgttc tcgcggccat      720
aacaaccgac gtacggcgtt cgcccctcgc cggcaacaaa aagccacgga agtccgcctg      780
gagcagaaaa tgcccacgct actgcgggtt tatatagacg gtccccacgg gatggggaaa      840
accaccacca cgcaactgct ggtggccctg ggttcgcgcg acgatatcgt ctacgtaccc      900
gagccgatga cttactggcg ggtgttgggg gcttccgaga caatcgcgaa catctacacc      960
acacaacacc gcctcgacca gggtgagata tcggccgggg acgcggcggt ggtaatgaca     1020
agcgcccaga taacaatggg catgccttat gccgtgaccg acgccgttct ggctcctcat     1080
atcggggggg aggctgggag ctcacatgcc ccgcccccgg ccctcaccct catcttcgac     1140
cgccatccca tcgccgccct cctgtgctac ccggccgcgc gataccttat gggcagcatg     1200
accccccagg ccgtgctggc gttcgtggcc ctcatcccgc cgaccttgcc cggcacaaac     1260
atcgtgttgg gggcccttcc ggaggacaga cacatcgacc gcctggccaa acgccagcgc     1320
cccggcgagc ggcttgacct ggctatgctg ccgcgattcc gccgcgttta tgggctgctt     1380
gccaatacgg tgcggtatct gcagggcggc gggtcgtggc gggaggattg gggacagctt     1440 tcggggcgg ccgtgccgcc ccagggtgcc gagcccccaga gcaacgcggg cccacgaccc     1500
catatcgggg acacgttatt taccctgttt cgggcccccg agttgctggc ccccaacggc     1560
gacctgtata acgtgtttgc ctgggctttg gacgtcttgg ccaaacgcct ccgtcccatg     1620
catgtcttta tcctggatta cgaccaatcg cccgccggct gccgggacgc cctgctgcaa     1680
cttacctccg ggatggtcca gacccacgtc accaccccag gctccatacc gacgatctgc     1740
gacctggcgc gcacgtttgc ccgggagatg ggggaggcta actgactaat aagtgtcaga     1800
tagcaatttg cacaagaaat caataccagc aactgtaaat aagcgctgaa gtgaccatgc     1860
catgctacga aagagcagaa aaaaacctgc cgtagaaccg aagagatatg acacgcttcc     1920
atctctcaaa ggaagaatcc cttcagggtt gcgtttccag gcggccgcaa attacatgt      1979
```

<210> SEQ ID NO 20
<211> LENGTH: 2000
<212> TYPE: DNA
<213> ORGANISM: Artificial Sequence
<220> FEATURE:
<223> OTHER INFORMATION: 5'-terminal flanking sequence of glycosylase
      gene

<400> SEQUENCE: 20

```
ctaccaatgc tctcgaggat tgcctgaaca ttgacattcg gcgtccggcc gggaccaccg       60
cggactcgaa gctgcctgtg ctggtctgga tctttggcgg aggctttgaa cttggttcaa      120
aggcgatgta tgatggtaca acgatggtat catcgtcgat agacaagaac atgcctatcg      180
tgtttgtagc aatgaattat cgcgtgggag gtttcgggtt cttgcccgga aaggagatcc      240
tggaggacgg gtccgcgaac ctagggctcc tggaccaacg ccttgccctg cagtgggttg      300
ccgacaacat cgaggccttt ggtggagacc cggacaaggt gacgatttgg ggagaatcag      360
caggagccat ttccgttttt gatcagatga tcttgtacga cggaaacatc acttacaagg      420
ataagcccct tgttccgggg gccatcatgg actccggtag tgttgttccc gcagaccccg      480
tcgatggggt caagggacag caagtatatg atgcggtagt ggaatctgca ggctgttcct      540
```

```
cttctaacga caccctagct tgtctgcgtg aactagacta caccgacttc ctcaatgcgg    600
caaactccgt gccaggcatt ttaagctacc attctgtggc gttatcatat gtgcctcgac    660
cggacgggac ggcgttgtcg gcatcaccgg acgttttggg caaagcaggg aaatatgctc    720
gggtcccgtt catcgtgggc gaccaagagg atgaggggac cttattcgcc ttgtttcagt    780
ccaacattac gacgatcgac gaggtggtcg actacctggc ctcatacttc ttctatgacg    840
ctagccgaga gcagcttgaa gaactagtgg ccctgtaccc agacaccacc acgtacgggt    900
ctccgttcag gacaggcgcg gccaacaact ggtatccgca atttaagcga ttggccgcca    960
ttctcggcga cttggtcttc accattaccc ggcgggcatt cctctcgtat gcagaggaaa   1020
tctcccctga tcttccgaac tggtcgtacc tggcgaccta tgactatggc accccagttc   1080
tggggacctt ccacggaagt gacctgctgc aggtgttcta tgggatcaag ccaaactatg   1140
cagctagttc tagccacacg tactatctga gctttgtgta tacgctggat ccgaactcca   1200
accgggggga gtacattgag tggccgcagt ggaaggaatc gcggcagttg atgaatttcg   1260
gagcgaacga cgccagtctc cttacggatg atttccgcaa cgggacatat gagttcatcc   1320
tgcagaatac cgcggcgttc cacatctgat gccattggcg gaggggtccg gacggtcagg   1380
aacttagcct tatgagatga atgatggacg tgtctggcct cggaaaagga tatatgggga   1440
tcatgatagt actagccata ttaatgaagg gcatatacca gcgttggac ctgcgttata   1500
gcttcccgtt agttatagta ccatcgttat accagccaat caagtcacca cgcacgaccg   1560
gggacggcga atccccggga attgaaagaa attgcatccc aggccagtga ggccagcgat   1620
tggccacctc tccaaggcac agggccattc tgcagcgctg gtggattcat cgcaatttcc   1680
cccggcccgg cccgacaccg ctataggctg gttctcccac accatcggag attcgtcgcc   1740
taatgtctcg tccgttcaca agctgaagag cttgaagtgg cgagatgtct ctgcaggaat   1800
tcaagctaga tgctaagcga tattgcatgg caatatgtgt tgatgcatgt gcttcttcct   1860
tcagcttccc ctcgtgcaga tgaggtttgg ctataaattg aagtggttgg tcggggttcc   1920
gtgaggggct gaagtgcttc ctccctttta gacgcaactg agagcctgag cttcatcccc   1980
agcatcatta cacctcagca                                               2000
```

<210> SEQ ID NO 21
<211> LENGTH: 2000
<212> TYPE: DNA
<213> ORGANISM: Aspergillus niger

<400> SEQUENCE: 21

```
acaatcaatc catttcgcta tagttaaagg atggggatga gggcaattgg ttatatgatc     60
atgtatgtag tgggtgtgca taatagtagt gaaatggaag ccaagtcatg tgattgtaat    120
cgaccgacgg aattgaggat atccggaaat acagacaccg tgaaagccat ggtctttcct    180
tcgtgtagaa gaccagacag acagtccctg atttacccct gcacaaagca ctagaaaatt    240
agcattccat ccttctctgc ttgctctgct gatatcactg tcattcaatg catagccatg    300
agctcatctt agatccaagc acgtaattcc atagccgagg tccacagtgg agcagcaaca    360
ttccccatca ttgctttccc caggggcctc ccaacgacta aatcaagagt atatctctac    420
cgtccaatag atcgtcttcg cttcaaaatc tttgacaatt ccaagagggt ccccatccat    480
caaacccagt tcaataatag ccagagatgc tggtggagtc aattaggcag tattgctgga    540
atgtcggggc cagttggccc ggtggtcatt ggccgcctgt gatgccatct ccactaaat    600
ccgatcattg atccaccgcc cacgaggcgc gtctttgctt tttgcgcggc gtccaggttc    660
```

```
aactctctct gcagctccag tccaacgctg actgactagt ttacctactg gtctgatcgg    720
ctccatcaga gctatggcgt tatcccgtgc cgttgctgcg caatcgctat cttgatcgca    780
accttgaact cactcttgtt ttaatagtga tcttggtgac ggagtgtcgg tgagtgacaa    840
ccaacatcgt gcaagggaga ttgatacgga attgtcgctc ccatcatgat gttcttgccg    900
gctttgttgg ccctattcgt gggatgcgat gccctcgctg tgcagcagca ggtactgctg    960
gatgaggagc catcggtctc tgcacgcaaa cccaacttcc tcttcattct cacggatgat   1020
caggatctcc ggatgaattc tccggcgtat atgccgtata cgcaggcgag aatcaaggaa   1080
aagggtaccg agttcttgaa ccatttcgtc actaccgcgc tttgctgtcc gtcgcgcgtg   1140
agtctttgga cgggaagaca ggctcataat actaatgtga cggatgtgaa cccgccttat   1200
ggtatggaca ctgcttcgat cggtcttgat tcttcagcgt ggttacaatt gctaatgcgg   1260
cataggcgga taccccaaat tcgtcgctca aggcttcaac gaaaacttcc tccccgtttg   1320
gctgcagtcc gccggttaca atacctacta cacggggaag ctgttcaact cgcacagtgt   1380
cgctacctat aacgcgccct tgtgaacgg tttcaatggc tccgacttcc tcctcgaccc   1440
ccacacatat tcctactgga atgcgacata ccagcgaaac catgagcctc cgcggagtta   1500
cgagggacaa tatactacgg atgtgatgaa ggagaaggca tcgggattgt tggcagatgc   1560
gctggacagt gacgcgccat tcttcctgac ggtcgcgccg atcgcaccgc acacgaacat   1620
cgatgtggag gggctgagcg tgcgggtgg accgaagatg acagagccgc tgcctgcacc   1680
gagacatgcg catttgtttg ctgatgcaaa ggtgccgcgg acgcctaatt tcaatccgga   1740
caaggtgtgt gatatcctga cacagtggtg gggacgggca ctgacaagag taggattctg   1800
gtgcggggtg gatccaaacc atggaactac agaaccagac cgtcatcgac tacgaagacc   1860
atctttatcg ccagcgtctg cgcactttgc aagccgtcga tgagatggtg gatgcgctga   1920
tcacgcagct ggaagaaagt gggcagatcg acaataccta catcatttac agtgctgata   1980
acggctacca cattggccat                                               2000

<210> SEQ ID NO 22
<211> LENGTH: 2480
<212> TYPE: DNA
<213> ORGANISM: Aspergillus niger

<400> SEQUENCE: 22
tgccattggc ggaggggtcc ggacggtcag gaacttagcc ttatgagatg aatgatggac     60
gtgtctggcc tcggaaaagg atatatgggg atcatgatag tactagccat attaatgaag    120
ggcatatacc acgcgttgga cctgcgttat agcttcccgt tagttatagt accatcgtta    180
taccagccaa tcaagtcacc acgcacgacc ggggacggcg aatccccggg aattgaaaga    240
aattgcatcc caggccagtg aggccagcga ttggccacct ctccaaggca cagggccatt    300
ctgcagcgct ggtggattca tcgcaatttc ccccggcccg gcccgacacc gctataggct    360
ggttctccca caccatcgga gattcgtcgc ctaatgtctc gtccgttcac aagctgaaga    420
gcttgaagtg gcgagatgtc tctgcaggaa ttcaagctag atgctaagcg atattgcatg    480
gcaatatgtg ttgatgcatg tgcttcttcc ttcagcttcc cctcgtgcag atgaggtttg    540
gctataaatt gaagtggttg gtcgggggttc cgtgaggggc tgaagtgctt cctccctttt    600
agacgcaact gagagcctga gcttcatccc cagcatcatt acacctcagc aatgtcagat    660
atgaaaagcg gaaacatatc gatgaaagcg atcttaatcc cattttttatc tcttctgatt    720
```

```
ccgttaaccc cgcaatctgc attcgctcag agtgagccgg agctgaagct ggaaagtgtg      780
gtgattgtca gtcgtcatgg tgtgcgtgct ccaaccaagg ccacgcaact gatgcaggat      840
gtcaccccag acgcatggcc aacctggccg gtaaaactgg gttggctgac accgcgcggt      900
ggtgagctaa tcgcctatct cggacattac caacgccagc gtctggtagc cgacggattg      960
ctggcgaaaa agggctgccc gcagtctggt caggtcgcga ttattgctga tgtcgacgag     1020
cgtacccgta aaacaggcga agccttcgcc gccgggctgg cacctgactg tgcaataacc     1080
gtacataccc aggcagatac gtccagtccc gatccgttat ttaatcctct aaaaactggc     1140
gtttgccaac tggataactc gaacgtgact gacgcgatcc tcagcagggc aggagggtca     1200
attgctgact ttaccgggca tcggcaaacg gcgtttcgcg aactggaacg ggtgcttaat     1260
tttccgcaat caaacttgtg ccttaaacgt gagaaacagg acgaaagctg ttcattaacg     1320
caggcattac catcggaact caaggtgagc gccgacaatg tctcattaac cggtgcggta     1380
agcctcgcat caatgctgac ggagatattt ctcctgcaac aagcacaggg aatgccggag     1440
ccggggtggg aaggatcac cgattcacac cagtggaaca ccttgctaag tttgcataac     1500
gcgcaatttt atttgctaca acgcacgcca gaggttgccc gcagccgcgc caccccgtta     1560
ttagatttga tcaagacagc gttgacgccc catccaccgc aaaaacaggc gtatggtgtg     1620
acattaccca cttcagtgct gtttatcgcc ggacacgata ctaatctggc aaatctcggc     1680
ggcgcactgg agctcaactg gacgcttccc ggtcagccgg ataacacgcc gccaggtggt     1740
gaactggtgt ttgaacgctg gcgtcggcta agcgataaca gccagtggat tcaggtttcg     1800
ctggtcttcc agactttaca gcagatgcgt gataaaacgc cgctgtcatt aaatacgccg     1860
cccggagagg tgaaactgac cctggcagga tgtgaagagc gaaatgcgca gggcatgtgt     1920
tcgttggcag gttttacgca aatcgtgaat gaagcacgca taccggcgtg cagtttgtaa     1980
tgccattggc ggaggggtcc ggacggtcag gaacttagcc ttatgagatg aatgatggac     2040
gtgtctggcc tcgaaaaggg atatatgggg atcatgatag tactagccat attaatgaag     2100
ggcatatacc acgcgttgga cctgcgttat agcttcccgt tagttatagt accatcgtta     2160
taccagccaa tcaagtcacc acgcacgacc ggggacggcg aatccccggg aattgaaaga     2220
aattgcatcc caggccagtg aggccagcga ttggccacct ctccaaggca cagggccatt     2280
ctgcagcgct ggtggattca tcgcaatttc ccccggcccg gcccgacacc gctataggct     2340
ggttctccca caccatcgga gattcgtcgc ctaatgtctc gtccgttcac aagctgaaga     2400
gcttgaagtg gcgagatgtc tctgcaggaa ttcaagctag atgctaagcg atattgcatg     2460
gcaatatgtg ttgatgcatg                                                2480

<210> SEQ ID NO 23
<211> LENGTH: 2459
<212> TYPE: DNA
<213> ORGANISM: Aspergillus niger

<400> SEQUENCE: 23
tgccattggc ggaggggtcc ggacggtcag gaacttagcc ttatgagatg aatgatggac       60
gtgtctggcc tcgaaaaggg atatatgggg atcatgatag tactagccat attaatgaag      120
ggcatatacc acgcgttgga cctgcgttat agcttcccgt tagttatagt accatcgtta      180
taccagccaa tcaagtcacc acgcacgacc ggggacggcg aatccccggg aattgaaaga      240
aattgcatcc caggccagtg aggccagcga ttggccacct ctccaaggca cagggccatt      300
ctgcagcgct ggtggattca tcgcaatttc ccccggcccg gcccgacacc gctataggct      360
```

-continued

```
ggttctccca caccatcgga gattcgtcgc ctaatgtctc gtccgttcac aagctgaaga      420
gcttgaagtg gcgagatgtc tctgcaggaa ttcaagctag atgctaagcg atattgcatg      480
gcaatatgtg ttgatgcatg tgcttcttcc ttcagcttcc cctcgtgcag atgaggtttg      540
gctataaatt gaagtggttg gtcggggttc cgtgaggggc tgaagtgctt cctcccttt      600
agacgcaact gagagcctga gcttcatccc cagcatcatt acacctcagc aatgtcgttc      660
cgatctctac tcgccctgag cggcctcgtc tgcacagggt tggcaaatgt gatttccaag      720
cgcgcgcaga gtgagccgga gctgaagctg aaagtgtgg tgattgtcag tcgtcatggt       780
gtgcgtgctc caaccaaggc cacgcaactg atgcaggatc caccccaga cgcatggcca       840
acctggccgg taaaactggg ttggctgaca ccgcgcggtg gtgagctaat cgcctatctc      900
ggacattacc aacgcagcg tctggtagcc gacggattgc tggcgaaaaa gggctgcccg       960
cagtctggtc aggtcgcgat tattgctgat gtcgacgagc gtaccgtaa acaggcgaa       1020
gccttcgccg ccgggctggc acctgactgt gcaataaccg tacatacca ggcagatacg      1080
tccagtcccg atccgttatt taatcctcta aaaactggcg tttgccaact ggataactcg     1140
aacgtgactg acgcgatcct cagcagggca ggagggtcaa ttgctgactt taccgggcat     1200
cggcaaacgg cgtttcgcga actggaacgg gtgcttaatt ttccgcaatc aaacttgtgc    1260
cttaaacgtg agaaacagga cgaaagctgt tcattaacgc aggcattacc atcggaactc    1320
aaggtgagcg ccgacaatgt ctcattaacc ggtgcggtaa gcctcgcatc aatgctgacg    1380
gagatatttc tcctgcaaca agcacaggga atgccgagc cggggtgggg aaggatcacc     1440
gattcacacc agtggaacac cttgctaagt ttgcataacg cgcaatttta tttgctacaa    1500
cgcacgccag aggttgcccg cagccgcgcc accccgttat tagatttgat caagacagcg    1560
ttgacgcccc atccaccgca aaaacaggcg tatggtgtga cattacccac ttcagtgctg    1620
tttatcgccg gacacgatac taatctggca aatctcggcg gcgcactgga gctcaactgg    1680
acgcttcccg gtcagccgga taacacgccg ccaggtggtg aactggtgtt tgaacgctgg    1740
cgtcggctaa gcgataacag ccagtggatt caggtttcgc tggtcttcca gactttacag    1800
cagatgcgtg ataaaacgcc gctgtcatta atacgccgc ccggagaggt gaaactgacc    1860
ctggcaggat gtgaagagcg aaatgcgcag ggcatgtgtt cgttggcagg tttttacgcaa   1920
atcgtgaatg aagcacgcat accggcgtgc agtttgtaat gccattggcg gaggggtccg    1980
gacggtcagg aacttagcct tatgagatga atgatggacg tgtctggcct cggaaaagga    2040
tatatgggga tcatgatagt actagccata ttaatgaagg gcatatacca cgcgttggac    2100
ctgcgttata gcttcccgtt agttatagta ccatcgttat accagccaat caagtcacca    2160
cgcacgaccg gggacggcga atccccggga attgaaagaa attgcatccc aggccagtga    2220
ggccagcgat tggccaccct tccaaggcac agggccattc tgcagcgctg gtggattcat    2280
cgcaatttcc cccggcccgg cccgacaccg ctataggctg gttctcccac accatcggag    2340
attcgtcgcc taatgtctcg tccgttcaca agctgaagag cttgaagtgg cgagatgtct    2400
ctgcaggaat tcaagctaga tgctaagcga tattgcatgg caatatgtgt tgatgcatg    2459
```

<210> SEQ ID NO 24
<211> LENGTH: 2468
<212> TYPE: DNA
<213> ORGANISM: Aspergillus niger

<400> SEQUENCE: 24

```
tgccattggc ggaggggtcc ggacggtcag gaacttagcc ttatgagatg aatgatggac      60
gtgtctggcc tcggaaaagg atatatgggg atcatgatag tactagccat attaatgaag     120
ggcatatacc acgcgttgga cctgcgttat agcttcccgt tagttatagt accatcgtta     180
taccagccaa tcaagtcacc acgcacgacc ggggacggcg aatccccggg aattgaaaga     240
aattgcatcc caggccagtg aggccagcga ttggccacct ctccaaggca cagggccatt     300
ctgcagcgct ggtggattca tcgcaatttc ccccggcccg gcccgacacc gctataggct     360
ggttctccca caccatcgga gattcgtcgc ctaatgtctc gtccgttcac aagctgaaga     420
gcttgaagtg gcgagatgtc tctgcaggaa ttcaagctag atgctaagcg atattgcatg     480
gcaatatgtg ttgatgcatg tgcttcttcc ttcagcttcc cctcgtgcag atgaggtttg     540
gctataaatt gaagtggttg gtcggggttc cgtgaggggc tgaagtgctt cctccctttt     600
agacgcaact gagagcctga gcttcatccc cagcatcatt acacctcagc aatggtcgcc     660
tggtggtccc tcttcctcta cggtctccag gtcgccgccc ccgccctcgc cgccacccc      720 gccgactggc gctcccagag tgagccgagc tgaagctgg aaagtgtggt gattgtcagt      780
cgtcatggtg tgcgtgctcc aaccaaggcc acgcaactga tgcaggatgt caccccagac     840
gcatggccaa cctggccggt aaaactgggt tggctgacac cgcgcggtgg tgagctaatc     900
gcctatctcg acattacca acgccagcgt ctggtagccg acggattgct ggcgaaaaag      960
ggctgcccgc agtctggtca ggtcgcgatt attgctgatg tcgacgagcg tacccgtaaa    1020
acaggcgaag ccttcgccgc cgggctggca cctgactgtg caataaccgt atacccag     1080 gcagatacgt ccagtcccga tccgttattt aatcctctaa aaactggcgt ttgccaactg    1140
gataactcga acgtgactga cgcgatcctc agcagggcag gagggtcaat tgctgacttt    1200
accgggcatc ggcaaacggc gtttcgcgaa ctggaacggg tgcttaattt tccgcaatca    1260
aacttgtgcc ttaaacgtga gaaacaggac gaaagctgtt cattaacgca ggcattacca    1320
tcggaactca aggtgagcgc cgacaatgtc tcattaaccg gtgcggtaag cctcgcatca    1380
atgctgacgg agatatttct cctgcaacaa gcacagggaa tgccggagcc ggggtgggga    1440
aggatcaccg attcacacca gtggaacacc ttgctaagtt tgcataacgc gcaatttat     1500 ttgctacaac gcacgccaga ggttgcccgc agccgcgcca ccccgttatt agatttgatc    1560
aagacagcgt tgacgcccca tccaccgcaa aaacaggcgt atggtgtgac attacccact    1620
tcagtgctgt ttatcgccgg acacgatact aatctggcaa atctcggcgg cgcactggag    1680
ctcaactgga cgcttcccgg tcagccggat aacacgccgc caggtggtga actggtgttt    1740
gaacgctggc gtcggctaag cgataacagc cagtggattc aggtttcgct ggtcttccag    1800
actttacagc agatgcgtga taaaacgccg ctgtcattaa atacgccgcc cggagaggtg    1860
aaactgaccc tggcaggatg tgaagagcga aatgcgcagg gcatgtgttc gttggcaggt    1920
tttacgcaaa tcgtgaatga agcacgcata ccggcgtgca gtttgtaatg ccattggcgg    1980
aggggtccgg acgtcagga acttagcctt atgagatgaa tgatggacgt gtctggcctc    2040
ggaaaaggat atatggggat catgatagta ctagccatat taatgaaggg catataccac    2100
gcgttggacc tgcgttatag cttcccgtta gttatagtac catcgttata ccagccaatc    2160
aagtcaccac gcacgaccgg ggacggcgaa tccccgggaa ttgaaagaaa ttgcatccca    2220
ggccagtgag gccagcgatt ggccacctct ccaaggcaca gggccattct gcagcgctgg    2280
tggattcatc gcaatttccc ccggcccggc ccgacaccgc tataggctgg ttctcccaca    2340
ccatcggaga ttcgtcgcct aatgtctcgt ccgttcacaa gctgaagagc ttgaagtggc    2400
```

```
gagatgtctc tgcaggaatt caagctagat gctaagcgat attgcatggc aatatgtgtt    2460
gatgcatg                                                              2468

<210> SEQ ID NO 25
<211> LENGTH: 2480
<212> TYPE: DNA
<213> ORGANISM: Aspergillus niger

<400> SEQUENCE: 25
tgccattggc ggaggggtcc ggacggtcag gaacttagcc ttatgagatg aatgatggac      60
gtgtctggcc tcggaaaagg atatatgggg atcatgatag tactagccat attaatgaag     120
ggcatatacc acgcgttgga cctgcgttat agcttcccgt tagttatagt accatcgtta     180
taccagccaa tcaagtcacc acgcacgacc ggggacggcg aatccccggg aattgaaaga     240
aattgcatcc caggccagtg aggccagcga ttggccacct ctccaaggca cagggccatt     300
ctgcagcgct ggtggattca tcgcaatttc cccggcccg gccgacacc gctataggct       360 ggttctccca caccatcgga gattcgtcgc ctaatgtctc gtccgttcac aagctgaaga     420
gcttgaagtg gcgagatgtc tctgcaggaa ttcaagctag atgctaagcg atattgcatg     480
gcaatatgtg ttgatgcatg tgcttcttcc ttcagcttcc cctcgtgcag atgaggtttg     540
gctataaatt gaagtggttg gtcggggttc cgtgaggggc tgaagtgctt cctcccttt      600 agacgcaact gagagcctga gcttcatccc cagcatcatt acacctcagc aatgtccgac     660
atgaagtccg gtaacatctc catgaaggcc atcctgatcc ccttcctgtc cctgctgatc     720
cccctgaccc cccagtccgc cttcgcccag tccgagcccg agctcaagct cgagtccgtc     780
gtcatcgtct cccgccacgg tgtccgcgcc cccaccaagg ccacccagct catgcaggac     840 gtcaccccg acgcctggcc cacctggccc gtcaagctcg gttggctcac ccccgcggt       900 ggtgagctca tcgcctacct cggtcactac cagcgccagc gcctcgtcgc cgacggtctc     960
ctcgccaaga agggttgccc ccagtccggt caggtcgcca tcatcgccga cgtcgacgag    1020
cgcacccgca agaccggtga ggccttcgcc gccggtctcg cccccgactg cgccatcacc    1080
gtccacaccc aggccgacac ctcctccccc gaccccctct tcaaccccct caagaccggt    1140
gtctgccagc tcgacaactc caacgtcacc gacgccatcc tctcccgcgc cggtggttcc    1200
atcgccgact tcaccggtca ccgccagacc gccttccgcg agctcgagcg cgtcctcaac    1260
ttcccccagt ccaacctctg cctcaagcgc gagaagcagg acgagtcctg ctccctcacc    1320
caggccctcc cctccgagct caaggtctcc gccgacaacg tctccctcac cggtgccgtc    1380
tccctcgcct ccatgctcac cgagatcttc ctcctccagc aggcccaggg tatgcccgag    1440
cccggttggg gtcgcatcac cgactccac cagtggaaca ccctcctctc cctccacaac    1500
gcccagttct acctcctcca gcgcaccccc gaggtcgccc gctcccgcgc cacccccctc    1560
ctcgacctca tcaagaccgc cctcaccccc caccccccc agaagcaggc ctacggtgtc    1620
accctcccca cctccgtcct cttcatcgcc ggtcacgaca ccaacctcgc caacctcggt    1680
ggtgccctcg agctcaactg gacccctccc ggtcagcccg acaacacccc ccccggtggt    1740
gagctcgtct cgagcgctg gcgccgcctc tccgacaact cccagtggat ccaggtctcc    1800
ctcgtcttcc agaccctcca gcagatgcgc gacaagaccc ccctctccct caacacccc    1860 cccggtgagg tcaagctcac cctcgccggt tgcgaggagc gcaacgccca gggtatgtgc    1920
tccctcgccg gtttcaccca gatcgtcaac gaggcccgca tccccgcctg ctccctctaa    1980
```

```
tgccattggc ggaggggtcc ggacggtcag gaacttagcc ttatgagatg aatgatggac    2040
gtgtctggcc tcggaaaagg atatatgggg atcatgatag tactagccat attaatgaag    2100
ggcatatacc acgcgttgga cctgcgttat agcttcccgt tagttatagt accatcgtta    2160
taccagccaa tcaagtcacc acgcacgacc ggggacggcg aatccccggg aattgaaaga    2220
aattgcatcc caggccagtg aggccagcga ttggccacct ctccaaggca cagggccatt    2280
ctgcagcgct ggtggattca tcgcaatttc ccccggcccg gccgacacc gctataggct     2340
ggttctccca caccatcgga gattcgtcgc ctaatgtctc gtccgttcac aagctgaaga    2400
gcttgaagtg gcgagatgtc tctgcaggaa ttcaagctag atgctaagcg atattgcatg    2460
gcaatatgtg ttgatgcatg                                                2480
```

<210> SEQ ID NO 26
<211> LENGTH: 2459
<212> TYPE: DNA
<213> ORGANISM: Aspergillus niger

<400> SEQUENCE: 26

```
tgccattggc ggaggggtcc ggacggtcag gaacttagcc ttatgagatg aatgatggac      60
gtgtctggcc tcggaaaagg atatatgggg atcatgatag tactagccat attaatgaag     120
ggcatatacc acgcgttgga cctgcgttat agcttcccgt tagttatagt accatcgtta     180
taccagccaa tcaagtcacc acgcacgacc ggggacggcg aatccccggg aattgaaaga     240
aattgcatcc caggccagtg aggccagcga ttggccacct ctccaaggca cagggccatt     300
ctgcagcgct ggtggattca tcgcaatttc ccccggcccg gccgacacc gctataggct      360
ggttctccca caccatcgga gattcgtcgc ctaatgtctc gtccgttcac aagctgaaga     420
gcttgaagtg gcgagatgtc tctgcaggaa ttcaagctag atgctaagcg atattgcatg     480
gcaatatgtg ttgatgcatg tgcttcttcc ttcagcttcc cctcgtgcag atgaggtttg     540
gctataaatt gaagtggttg gtcggggttc cgtgagggc tgaagtgctt cctccctttt      600
agacgcaact gagagcctga gcttcatccc cagcatcatt acacctcagc aatgtcgttc     660
cgatctctac tcgccctgag cggcctcgtc tgcacagggt tggcaaatgt gatttccaag    720
cgcgcgcagt ccgagcccga gctcaagctc gagtccgtcg tcatcgtctc ccgccacggt    780
gtccgcgccc ccaccaaggc cacccagctc atgcaggacg tcaccccga cgcctggccc     840
acctggcccg tcaagctcgg ttggctcacc ccccgcggtg gtgagctcat cgcctacctc    900
ggtcactacc agcgccagcg cctcgtcgcc gacggtctcc tcgccaagaa gggttgcccc    960
cagtccggtc aggtcgccat catcgccgac gtcgacgagc gcacccgcaa gaccggtgag   1020
gccttcgccg ccggtctcgc ccccgactgc gccataccg tccacaccca ggccgacacc    1080
tcctcccccg accccctctt caaccccctc aagaccggtg tctgccagct cgacaactcc   1140
aacgtcaccg acgccatcct ctcccgcgcc ggtggttcca tcgccgactt caccggtcac   1200
cgccagaccg ccttccgcga gctcgagcgc gtcctcaact tccccagtc caacctctgc    1260
ctcaagcgcg agaagcagga cgagtcctgc tccctcaccc aggccctccc ctccgagctc   1320
aaggtctccg ccgacaacgt ctccctcacc ggtgccgtct ccctcgcctc catgctcacc   1380
gagatcttcc tcctccagca ggcccagggt atgcccgagc ccggttgggg tcgcatcacc   1440
gactcccacc agtggaacac cctctctctc ctcacaacg cccagttcta cctcctccag    1500
cgcacccccg aggtcgcccg ctcccgcgcc accccctcc tcgacctcat caagaccgcc    1560
ctcacccccc acccccccca gaagcaggcc tacggtgtca ccctcccac ctccgtcctc    1620
```

```
ttcatcgccg gtcacgacac caacctcgcc aacctcggtg gtgccctcga gctcaactgg   1680
accctccccg gtcagcccga caacaccccc cccggtggtg agctcgtctt cgagcgctgg   1740
cgccgcctct ccgacaactc ccagtggatc caggtctccc tcgtcttcca gaccctccag   1800
cagatgcgcg acaagacccc cctctccctc aacaccccc ccggtgaggt caagctcacc    1860
ctcgccggtt gcgaggagcg caacgcccag ggtatgtgct ccctcgccgg tttcacccag   1920
atcgtcaacg aggcccgcat ccccgcctgc tccctctaat gccattggcg aggggtccg    1980 gacggtcagg aacttagcct tatgagatga atgatggacg tgtctggcct cggaaaagga   2040
tatatgggga tcatgatagt actagccata ttaatgaagg gcatatacca cgcgttggac   2100
ctgcgttata gcttcccgtt agttatagta ccatcgttat accagccaat caagtcacca   2160
cgcacgaccg gggacggcga atccccggga attgaaagaa attgcatccc aggccagtga   2220
ggccagcgat tggccacctc tccaaggcac agggccattc tgcagcgctg gtggattcat   2280
cgcaatttcc cccggcccgg cccgacaccg ctataggctg gttctcccac accatcggag   2340
attcgtcgcc taatgtctcg tccgttcaca agctgaagag cttgaagtgg cgagatgtct   2400
ctgcaggaat tcaagctaga tgctaagcga tattgcatgg caatatgtgt tgatgcatg    2459
```

<210> SEQ ID NO 27
<211> LENGTH: 2468
<212> TYPE: DNA
<213> ORGANISM: Aspergillus niger

<400> SEQUENCE: 27

```
tgccattggc ggaggggtcc ggacggtcag gaacttagcc ttatgagatg aatgatggac     60
gtgtctggcc tcggaaaagg atatatgggg atcatgatag tactagccat attaatgaag    120
ggcatatacc acgcgttgga cctgcgttat agcttcccgt tagttatagt accatcgtta    180
taccagccaa tcaagtcacc acgcacgacc ggggacggcg aatccccggg aattgaaaga    240
aattgcatcc caggccagtg aggccagcga ttggccacct ctccaaggca cagggccatt    300
ctgcagcgct ggtggattca tcgcaatttc cccggcccg cccgacaccg ctataggct      360 ggttctccca ccatcggag attcgtcgc ctaatgtctc gtccgttcac aagctgaaga      420
gcttgaagtg gcgagatgtc tctgcaggaa ttcaagctag atgctaagcg atattgcatg    480
gcaatatgtg ttgatgcatg tgcttcttcc ttcagcttcc cctcgtgcag atgaggtttg    540
gctataaatt gaagtggttg gtcggggttc cgtgagggc tgaagtgctt cctccctttt     600
agacgcaact gagagcctga gcttcatccc cagcatcatt acacctcagc aatggtcgcc    660
tggtggtccc tcttcctcta cggtctccag gtcgccgccc ccgccctcgc cgccacccc    720 gccgactggc gctcccagtc cgagcccgag ctcaagctcg agtccgtcgt catcgtctcc    780
cgccacggtg tccgcgcccc caccaaggcc accagctca tgcaggacgt caccccgac     840 gcctggccca cctggcccgt caagctcggt tggctcaccc ccgcggtgg tgagctcatc      900 gcctacctcg gtcactacca gcgccagcgc ctcgtcgccg acggtctcct cgccaagaag    960
ggttgccccc agtccggtca ggtcgccatc atcgccgacg tcgacgagcg cacccgcaag   1020
accggtgagg ccttcgccgc cggtctcgcc cccgactgcg ccatcaccgt ccacacccag   1080
gccgacacct cctcccccga ccccctcttc aaccccctca agaccggtgt ctgccagctc   1140
gacaactcca cgtcaccga cgccatcctc tcccgcgccg tggttccat cgccgacttc   1200 accggtcacc gccagaccgc cttccgcgag ctcgagcgcg tcctcaactt cccccagtcc   1260
```

-continued

```
aacctctgcc tcaagcgcga gaagcaggac gagtcctgct ccctcaccca ggccctcccc    1320
tccgagctca aggtctccgc cgacaacgtc tccctcaccg gtgccgtctc cctcgcctcc    1380
atgctcaccg agatcttcct cctccagcag gcccagggta tgcccgagcc cggttggggt    1440
cgcatcaccg actcccacca gtggaacacc tcctctctcc tccacaacgc ccagttctac    1500
ctcctccagc gcaccccga ggtcgcccgc tcccgcgcca ccccctcct cgacctcatc     1560 aagaccgccc tcacccccca ccccccccag aagcaggcct acggtgtcac cctccccacc    1620
tccgtcctct tcatcgccgg tcacgacacc aacctcgcca acctcggtgg tgccctcgag    1680
ctcaactgga ccctcccgg tcagcccgac aacaccccc ccggtggtga gctcgtcttc      1740
gagcgctggc gccgcctctc cgacaactcc cagtggatcc aggtctccct cgtcttccag    1800
accctccagc agatgcgcga caagaccccc ctctccctca caccccccc cggtgaggtc     1860 aagctcaccc tcgccggttg cgaggagcgc aacgcccagg gtatgtgctc cctcgccggt    1920
ttcacccaga tcgtcaacga ggcccgcatc cccgcctgct ccctctaatg ccattggcgg    1980
aggggtccgg acggtcagga acttagcctt atgagatgaa tgatggacgt gtctggcctc    2040
ggaaaaggat atatggggat catgatagta ctagccatat taatgaaggg catataccac    2100
gcgttggacc tgcgttatag cttcccgtta gttatagtac catcgttata ccagccaatc    2160
aagtcaccac gcacgaccgg ggacggcgaa tccccgggaa ttgaaagaaa ttgcatccca    2220
ggccagtgag gccagcgatt ggccacctct ccaaggcaca gggccattct gcagcgctgg    2280
tggattcatc gcaatttccc ccggcccggc ccgacaccgc tataggctgg ttctcccaca    2340
ccatcggaga ttcgtcgcct aatgtctcgt ccgttcacaa gctgaagagc ttgaagtggc    2400
gagatgtctc tgcaggaatt caagctagat gctaagcgat attgcatggc aatatgtgtt    2460
gatgcatg                                                             2468
```

<210> SEQ ID NO 28
<211> LENGTH: 2468
<212> TYPE: DNA
<213> ORGANISM: Aspergillus niger

<400> SEQUENCE: 28

```
tgccattggc ggagggtcc ggacggtcag gaacttagcc ttatgagatg aatgatggac     60
gtgtctggcc tcggaaaagg atatatgggg atcatgatag tactagccat attaatgaag    120
ggcatatacc acgcgttgga cctgcgttat agcttcccgt tagttatagt accatcgtta    180
taccagccaa tcaagtcacc acgcacgacc ggggacggcg aatccccggg aattgaaaga    240
aattgcatcc caggccagtg aggccagcga ttggccacct ctccaaggca cagggccatt    300
ctgcagcgct ggtggattca tcgcaatttc cccggcccg gccgacacc gctataggct     360 ggttctccca ccatcggaga ttcgtcgc ctaatgtctc gtccgttcac aagctgaaga    420
gcttgaagtg gcgagatgtc tctgcaggaa ttcaagctag atgctaagcg atattgcatg    480
gcaatatgtg ttgatgcatg tgcttcttcc ttcagcttcc cctcgtgcag atgaggtttg    540
gctataaatt gaagtggttg gtcggggttc cgtgagggc tgaagtgctt cctcccttt    600 agacgcaact gagagcctga gcttcatccc cagcatcatt acacctcagc aatggtcgcc    660
tggtggtccc tcttcctcta cggtctccag gtcgccgccc ccgccctcgc cgccaccccc    720
gccgactggc gctcccagtc cgagcccgag ctcaagctcg agtccgtcgt catcgtctcc    780
cgccacggtg tccgcgcccc caccaaggcc acccagctca tgcaggacgt cacccccgac    840
gcctggccca cctggcccgt caagctcggt gagctcaccc ccgcggtgg tgagctcatc    900
```

```
gcctacctcg gtcactactg gcgccagcgc ctcgtcgccg acggtctcct ccccaagtgc    960
ggttgccccc agtccggtca ggtcgccatc atcgccgacg tcgacgagcg cacccgcaag   1020
accggtgagg ccttcgccgc cggtctcgcc cccgactgcg ccatcaccgt ccacacccag   1080
gccgacacct cctcccccga ccccctcttc aaccccctca agaccggtgt ctgccagctc   1140
gacaacgcca acgtcaccga cgccatcctc gagcgcgccg gtggttccat cgccgacttc   1200
accggtcact accagaccgc cttccgcgag ctcgagcgcg tcctcaactt cccccagtcc   1260
aacctctgcc tcaagcgcga gaagcaggac gagtcctgct ccctcaccca ggccctcccc   1320
tccgagctca aggtctccgc cgactgcgtc tccctcaccg gtgccgtctc cctcgcctcc   1380
atgctcaccg agatcttcct cctccagcag gcccagggta tgcccgagcc cggttggggt   1440
cgcatcaccg actcccacca gtggaacacc ctcctctccc tccacaacgc ccagttcgac   1500
ctcctccagc gcaccccga ggtcgcccgc tcccgcgcca ccccctcct cgacctcatc   1560
aagaccgccc tcaccccca ccccccccag aagcaggcct acggtgtcac cctccccacc   1620
tccgtcctct tcatcgccgg tcacgacacc aacctcgcca acctcggtgg tgccctcgag   1680
ctcaactgga ccctccccgg tcagcccgac aacaccccc ccggtggtga gctcgtcttc   1740
gagcgctggc gccgcctctc cgacaactcc cagtggatcc aggtctccct cgtcttccag   1800
accctccagc agatgcgcga caagaccccc ctctccctca caccccccc cggtgaggtc   1860
aagctcaccc tcgccggttg cgaggagcgc aacgcccagg gtatgtgctc cctcgccggt   1920
ttcacccaga tcgtcaacga ggcccgcatc cccgcctgct ccctctaatg ccattggcgg   1980
aggggtccgg acggtcagga acttagcctt atgagatgaa tgatggacgt gtctggcctc   2040
ggaaaaggat atatgtggat catgatagta ctagccatat taatgaaggg catataccac   2100
gcgttggacc tgcgttatag cttcccgtta gttatagtac catcgttata ccagccaatc   2160
aagtcaccac gcacgaccgg ggacggcgaa tccccgggaa ttgaaagaaa ttgcatccca   2220
ggccagtgag gccagcgatt ggccacctct ccaaggcaca gggccattct gcagcgctgg   2280
tggattcatc gcaatttccc ccggcccggc ccgacaccgc tataggctgg ttctcccaca   2340
ccatcggaga ttcgtcgcct aatgtctcgt ccgttcacaa gctgaagagc ttgaagtggc   2400
gagatgtctc tgcaggaatt caagctagat gctaagcgat attgcatggc aatatgtgtt   2460
gatgcatg                                                           2468
```

<210> SEQ ID NO 29
<211> LENGTH: 2468
<212> TYPE: DNA
<213> ORGANISM: Aspergillus niger

<400> SEQUENCE: 29

```
tgccattggc ggagggtcc ggacggtcag gaacttagcc ttatgagatg aatgatggac     60
gtgtctggcc tcggaaaagg atatatgggg atcatgatag tactagccat attaatgaag    120
ggcatatacc acgcgttgga cctgcgttat agcttcccgt tagttatagt accatcgtta    180
taccagccaa tcaagtcacc acgcacgacc ggggacggcg aatccccggg aattgaaaga    240
aattgcatcc caggccagtg aggccagcga ttggccacct ctccaaggca cagggccatt    300
ctgcagcgct ggtggattca tcgcaatttc cccggcccg gcccgacacc gctataggct    360
ggttctccca caccatcgga gattcgtcgc ctaatgtctc gtccgttcac aagctgaaga    420
gcttgaagtg gcgagatgtc tctgcaggaa ttcaagctag atgctaagcg atattgcatg    480
```

```
gcaatatgtg ttgatgcatg tgcttcttcc ttcagcttcc cctcgtgcag atgaggtttg    540
gctataaatt gaagtggttg gtcggggttc cgtgaggggc tgaagtgctt cctccctttt    600
agacgcaact gagagcctga gcttcatccc cagcatcatt acacctcagc aatggtcgcc    660
tggtggtccc tcttcctcta cggtctccag gtcgccgccc ccgccctcgc cgccaccccc    720
gccgactggc gctcccagtc cgagcccgag ctcaagctcg agtccgtcgt catcgtctcc    780
cgccacggtg tccgcgcccc caccaaggcc acccagctca tgcaggacgt caccccccgac   840
gcctggccca cctggcccgt caagctcggt gagctcaccc ccgcggtgg tgagctcatc    900
gcctacctcg gtcactactg cgccagcgc ctcgtcgccg acggtctcct ccccaagtgc    960
ggttgccccc agtccggtca ggtcgccatc atcgccgacg tcgacgagcg cacccgcaag    1020
accggtgagg ccttcgccgc cggtctcgcc cccgactgcg ccatcaccgt ccacacccag    1080
gccgacacct cctcccccga cccctcttc aacccctca agaccggtgt ctgccagctc      1140
gacaacgcca acgtcaccga cgccatcctc gagcgcgccg gtggttccat cgccgacttc    1200
accggtcact accagaccgc cttccgcgag ctcgagcgcg tcctcaactt cccccagtcc    1260
aacctctgcc tcaagcgcga gaagcaggac gagtcctgct ccctcaccca ggccctcccc    1320
tccgagctca aggtctccgc cgactgcgtc tccctcaccg gtgccgtctc cctcgcctcc    1380
atgctcaccg agatcttcct cctccagcag gcccagggta tgcccgagcc cggttggggt    1440
cgcatcaccg actcccacca gtggaacacc ctcctctccc tccacaacgc ccagttcgac    1500
ctcctccagc gcaccccga ggtcgcccgc tcccgcgcca ccccctcct cgacctcatc     1560
aagaccgccc tcacccccca cccccccag aagcaggcct acggtgtcac cctcccccacc   1620
tccgtcctct tcatcgccgg tcacgacacc aacctcgcca acctcggtgg tgccctcgag    1680
ctcaactgga ccctccccgg tcagcccgac aacaccccc ccggtggtga gctcgtcttc     1740
gagcgctggc gccgcctctc cgacaactcc cagtggatcc aggtctccct cgtcttccag    1800
accctccagc agatgcgcga caagaccccc ctctccctca cacccccccc cggtgaggtc    1860
aagctcaccc tcgccggttg cgaggagcgc aacgcccagg gtatgtgctc cctcgccggt    1920
ttcacccaga tcgtcaacga ggcccgcatc cccgcctgct ccctctaatg ccattggcgg    1980
aggggtccgg acgtcagga acttagcctt atgagatgaa tgatggacgt gtctggcctc    2040
ggaaaaggat atatggggat catgatagta ctagccatat taatgaaggg catataccac    2100
gcgttggacc tgcgttatag cttcccgtta gttatagtac catcgttata ccagccaatc    2160
aagtcaccac gcacgaccgg ggacggcgaa tccccgggaa ttgaaagaaa ttgcatccca    2220
ggccagtgag gccagcgatt ggccacctct ccaaggcaca gggccattct gcagcgctgg    2280
tggattcatc gcaatttccc ccggcccggc ccgacaccgc tataggctgg ttctcccaca    2340
ccatcggaga ttcgtcgcct aatgtctcgt ccgttcacaa gctgaagagc ttgaagtggc    2400
gagatgtctc tgcaggaatt caagctagat gctaagcgat attgcatggc aatatgtgtt    2460
gatgcatg                                                             2468
```

<210> SEQ ID NO 30
<211> LENGTH: 30
<212> TYPE: DNA
<213> ORGANISM: Artificial Sequence
<220> FEATURE:
<223> OTHER INFORMATION: vector-F

<400> SEQUENCE: 30
gtacagtgac cggtgactct ttctggcatg                                     30

<210> SEQ ID NO 31
<211> LENGTH: 25
<212> TYPE: DNA
<213> ORGANISM: Artificial Sequence
<220> FEATURE:
<223> OTHER INFORMATION: vector-R

<400> SEQUENCE: 31
gatgcattcg cgaggtaccg agctc                                              25

<210> SEQ ID NO 32
<211> LENGTH: 72
<212> TYPE: DNA
<213> ORGANISM: Artificial Sequence
<220> FEATURE:
<223> OTHER INFORMATION: Gla-5'-F

<400> SEQUENCE: 32
aattcgagct cggtacctcg cgaatgcatc ctaccaatgc tctcgaggat tgcctgaaca        60
ttgacattcg gc                                                            72

<210> SEQ ID NO 33
<211> LENGTH: 23
<212> TYPE: DNA
<213> ORGANISM: Artificial Sequence
<220> FEATURE:
<223> OTHER INFORMATION: Gla-5'-R

<400> SEQUENCE: 33
tgctgaggtg taatgatgct ggg                                                23

<210> SEQ ID NO 34
<211> LENGTH: 33
<212> TYPE: DNA
<213> ORGANISM: Artificial Sequence
<220> FEATURE:
<223> OTHER INFORMATION: Gla-3'-F

<400> SEQUENCE: 34
acaatcaatc catttcgcta tagttaaagg atg                                     33

<210> SEQ ID NO 35
<211> LENGTH: 56
<212> TYPE: DNA
<213> ORGANISM: Artificial Sequence
<220> FEATURE:
<223> OTHER INFORMATION: Gla-3'-R

<400> SEQUENCE: 35
catgccagaa agagtcaccg gtcactgtac atggccaatg tggtagccgt tatcag            56

<210> SEQ ID NO 36
<211> LENGTH: 59
<212> TYPE: DNA
<213> ORGANISM: Artificial Sequence
<220> FEATURE:
<223> OTHER INFORMATION: Phy-Phy-F

<400> SEQUENCE: 36
cttcatcccc agcatcatta cacctcagca atgtcagata tgaaaagcgg aaacatatc         59

<210> SEQ ID NO 37
<211> LENGTH: 53
<212> TYPE: DNA

```
<213> ORGANISM: Artificial Sequence
<220> FEATURE:
<223> OTHER INFORMATION: Phy-Phy-R

<400> SEQUENCE: 37
cctttaacta tagcgaaatg gattgattgt ttacaaactg cacgccggta tgc        53

<210> SEQ ID NO 38
<211> LENGTH: 128
<212> TYPE: DNA
<213> ORGANISM: Artificial Sequence
<220> FEATURE:
<223> OTHER INFORMATION: Gla-Phy-F

<400> SEQUENCE: 38
cttcatcccc agcatcatta cacctcagca atgtcgttcc gatctctact cgccctgagc  60
ggcctcgtct gcacagggtt ggcaaatgtg atttccaagc gcgcgcagag tgagccggag  120
ctgaagct                                                          128

<210> SEQ ID NO 39
<211> LENGTH: 137
<212> TYPE: DNA
<213> ORGANISM: Artificial Sequence
<220> FEATURE:
<223> OTHER INFORMATION: Amylase-Phy-F

<400> SEQUENCE: 39
cttcatcccc agcatcatta cacctcagca atggtcgcct ggtggtccct cttcctctac  60
ggtctccagg tcgccgcccc cgccctcgcc gccaccccg ccgactggcg ctcccagagt   120
gagccggagc tgaagct                                                137

<210> SEQ ID NO 40
<211> LENGTH: 148
<212> TYPE: DNA
<213> ORGANISM: Artificial Sequence
<220> FEATURE:
<223> OTHER INFORMATION: Phy-PhyOPT-F

<400> SEQUENCE: 40
cttcatcccc agcatcatta cacctcagca atgtccgaca tgaagtccgg taacatctcc  60
atgaaggcca tcctgatccc cttcctgtcc ctgctgatcc ccctgacccc ccagtccgcc  120
ttcgcccagt ccgagcccga gctgaagc                                    148

<210> SEQ ID NO 41
<211> LENGTH: 53
<212> TYPE: DNA
<213> ORGANISM: Artificial Sequence
<220> FEATURE:
<223> OTHER INFORMATION: Phy-PhyOPT-R

<400> SEQUENCE: 41
cctttaacta tagcgaaatg gattgattgt ttagagggag caggcgggga tgc         53

<210> SEQ ID NO 42
<211> LENGTH: 127
<212> TYPE: DNA
<213> ORGANISM: Artificial Sequence
<220> FEATURE:
<223> OTHER INFORMATION: Gla-PhyOPT-F

<400> SEQUENCE: 42
cttcatcccc agcatcatta cacctcagca atgtcgttcc gatctctact cgccctgagc  60
```

```
ggcctcgtct gcacagggtt ggcaaatgtg atttccaagc gcgcgcagtc cgagcccgag    120
ctcaagc                                                              127
```

<210> SEQ ID NO 43
<211> LENGTH: 136
<212> TYPE: DNA
<213> ORGANISM: Artificial Sequence
<220> FEATURE:
<223> OTHER INFORMATION: Amylase-PhyOPT-F

<400> SEQUENCE: 43

```
cttcatcccc agcatcatta cacctcagca atggtcgcct ggtggtccct cttcctctac    60
ggtctccagg tcgccgcccc cgccctcgcc gccaccccg ccgactggcg ctcccagtcc     120
gagcccgagc tcaagc                                                    136
```

<210> SEQ ID NO 44
<211> LENGTH: 53
<212> TYPE: DNA
<213> ORGANISM: Artificial Sequence
<220> FEATURE:
<223> OTHER INFORMATION: Phy-PhyOPT-R

<400> SEQUENCE: 44

```
cctttaacta tagcgaaatg gattgattgt ttacagggag caggcgggga tgc           53
```

<210> SEQ ID NO 45
<211> LENGTH: 25
<212> TYPE: DNA
<213> ORGANISM: Artificial Sequence
<220> FEATURE:
<223> OTHER INFORMATION: Phy-5test-F

<400> SEQUENCE: 45

```
aatcgtgtcc gcagatgtac ttcac                                          25
```

<210> SEQ ID NO 46
<211> LENGTH: 25
<212> TYPE: DNA
<213> ORGANISM: Artificial Sequence
<220> FEATURE:
<223> OTHER INFORMATION: Phy-5test-R

<400> SEQUENCE: 46

```
ataatcatcc actgcacctc agagc                                          25
```

<210> SEQ ID NO 47
<211> LENGTH: 25
<212> TYPE: DNA
<213> ORGANISM: Artificial Sequence
<220> FEATURE:
<223> OTHER INFORMATION: Phy-3test-F

```
<400> SEQUENCE: 47
tttcccagtc acgacgttgt aaaac                                        25

<210> SEQ ID NO 48
<211> LENGTH: 26
<212> TYPE: DNA
<213> ORGANISM: Artificial Sequence
<220> FEATURE:
<223> OTHER INFORMATION: Phy-3test-R

<400> SEQUENCE: 48
aactcgaaca gtgtaggtgc aatgtc                                       26
```

EXPRESSION OF PHYTASE IN *ASPERGILLUS NIGER*

CROSS-REFERENCE TO RELATED APPLICATION

This application is a Section 371 of International Application No. PCT/CN2018/081272, filed Mar. 30, 2018, which was published in the Chinese language on Oct. 4, 2018, under International Publication No. WO 2018/177402 A1, which claims priority under 35 U.S.C. § 119(b) to Chinese Application Nos. 201710203473.5, filed Mar. 30, 2017 and 201710741963.0, filed Aug. 25, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065824_4US1_Sequence_Listing" having a creating date of Jul. 27, 2021 and having a size of 69.8 kb. The sequence listing submitted via EFS-Web is part of the specification and is herein incorporated by reference in its entirety.

TECHNICAL FIELD

The present invention relates to the field of genetic engineering, and to the high-efficiency expression of phytase derived from Gram-negative bacteria, particularly *Escherichia coli* phytase, in filamentous fungi, especially *Aspergillus niger*.

BACKGROUND

Phytase, that is, myo-Inositol hexakisphosphate phosphohydrolase, is an orthophosphoric-monoester phosphohydrolase, which catalyzes the hydrolysis of phytic acid to produce lower inositol phosphate derivatives and inorganic phosphoric acid. In some instances, phytic acid can be hydrolyzed into free inositol. Phytic acid is the most abundant in the seeds of crops such as grains, beans and oil crops, and is present in an amount of up to 1% to 3%, accounting for 60% to 80% of the total phosphorus content in the plants. However, the phosphorus in physic acid cannot be directly absorbed and utilized, and needs to be hydrolyzed into inorganic phosphate in the digestive tract. Studies have shown that monogastric animals (for example, pigs, chickens, ducks, and gooses, etc.) have low utilization of phosphorus in phytic acid due to the lack of phytase. Meanwhile, the strong electronegativity of phytic acid causes it to form insoluble salts with a divalent or trivalent cation such as $Ca^{2+}$, $Zn^{2+}$, and $Fe^{2++}$, hindering the absorption of minerals in the small intestine. It also forms complexes with proteins, amino acids and fatty acids, affecting their absorption and utilization. Phytic acid also binds to pepsin, chymotrypsin, trypsin, and others to reduce the digestive enzyme activity. Therefore, the addition of phytase to feed for monogastric animals can increase the utilization of phosphorus in the feed, reduce the phosphorus content in the animal excrements, and increase the energy utilization rate of the proteins and the feed.

Commercial phytase is primarily derived from *Aspergillus niger* (as described in U.S. Pat. No. 5,436,156), *Escherichia coli* (as described in U.S. Pat. No. 7,432,098), *Citrobacter* genus (such as the *Citrobacter braakii* strain described in US 20100261259), and *Brucella* (such as *Buttiauxella* sp. described in U.S. Pat. No. 8,143,046) and so on. These phytases have different acid and heat resistances due to their different origins. Nielsen et al. (J Agric Food Chem. 2015, 63(3): 943-50) compared the performances of commercial phytases and showed that *Escherichia coli* phytase exhibits the best performances. Commercial *Escherichia coli* phytase products are all expressed in yeasts, such as schizosaccharomyces and *Pichia pastoris*, and most of the phytase products on the Chinese market are produced by *Pichia pastoris*. Since phytase is mainly used in the areas of feed and food, and *Pichia pastoris* needs to use methanol as a carbon source to induce protein expression when a protein is expressed in *Pichia pastoris*, it is difficult to completely remove methanol as a raw material from commercial phytase, thus causing potential safety hazards. In addition, due to the flammable and explosive nature of methanol, special safety protection is required during transportation and production, which increases the production costs. Moreover, higher requirements are imposed on the production environment, and there are certain potential hazards to the production workers. It is therefore not preferred to use *Pichia pastoris* to produce food and feed additives. Filamentous fungi are well known as cell factories for producing valuable products (such as enzymes). Among them, *Aspergillus niger* and *Aspergillus oryzae* are widely used as expression hosts because of their "Generally Recognized As Safe (GRAS)" characteristics. During the fermentation process, no toxic substances are produced, and the raw materials for fermentation are all cereals and by-products thereof (such as soybean meal, corn syrup, etc.). Therefore, *Aspergillus niger* and *Aspergillus oryzae* are more favored in the industry for the production of enzymes. It has been found through studies that the use of *Aspergillus niger* to express phytase derived from Gram-negative bacteria is difficult. For example, US 20100261259 describes the use of *Aspergillus oryzae*, *Aspergillus niger* and yeast to express *Citrobacter braakii* (a Gram-negative bacterium) phytase. The results show that *Aspergillus oryzae* and yeast can well secrete and express the phytase, while *Aspergillus niger* can hardly express the phytase. As described above, the phytase derived from the Gram-negative bacterium (*Escherichia coli*) and its mutant have better characteristics, and therefore the expression in *Aspergillus niger* that is GRAS is expected.

SUMMARY

An object of the present invention is to provide a signal peptide which enhances the secretory expression of *Escherichia coli* phytase or a mutant thereof in a filamentous fungus.

Another object of the present invention is to provide a codon-optimized gene encoding the *Escherichia coli* phytase or a mutant thereof.

Another object of the present invention is to provide a codon-optimized DNA sequence encoding the *Escherichia coli* phytase or a mutant mature peptide thereof.

A further object of the present invention is to provide a method for enhancing the secretory expression of the *Escherichia coli* phytase or a mutant thereof in a filamentous fungus.

The objects of the present invention can be accomplished through the following technical solutions:

In one aspect, the present invention provides a signal peptide for enhancing the secretory expression of *Escherichia coli* phytase or a mutant thereof in a filamentous fungus, where the signal peptide is selected from the *Aspergillus oryzae* TAKA amylase signal peptide having an amino acid sequence as shown in SEQ ID NO. 13.

In one embodiment of the present invention, the nucleotide sequence of the signal peptide is as shown in SEQ ID NO. 12.

In one embodiment of the present invention, the filamentous fungus is selected from *Aspergillus niger*.

In one embodiment of the present invention, the *Escherichia coli* phytase has an amino acid sequence as shown in SEQ ID NO. 4.

In another embodiment of the present invention, the mutant of the *Escherichia coli* phytase has an amino acid sequence as shown in SEQ ID NO. 15 or SEQ ID NO. 17.

In another aspect, the present invention provides a codon-optimized gene encoding *Escherichia coli* phytase or a mutant thereof, which has a nucleotide sequence as shown in SEQ ID NO. 7; or has a nucleotide sequence that is at least 95%, 96%, 97%, 98% or 99% homologous to the nucleotide sequence as shown in SEQ ID NO. 7, and encodes a protein having the phytase activity.

In one embodiment of the present invention, the *Escherichia coli* phytase has an amino acid sequence as shown in SEQ ID NO. 4.

In another embodiment of the present invention, the mutant of the *Escherichia coli* phytase has an amino acid sequence as shown in SEQ ID NO. 15 or SEQ ID NO. 17.

In still another aspect, the present invention provides a codon-optimized DNA sequence encoding *Escherichia coli* phytase or a mutant mature peptide thereof, which has a nucleotide sequence as shown in SEQ ID NO. 8, or has a nucleotide sequence that is at least 95%, 96%, 97%, 98% or 99% homologous to the nucleotide sequence as shown in SEQ ID NO. 8, and encodes a protein having the phytase activity.

In one embodiment of the present invention, the codon-optimized DNA sequence encoding *Escherichia coli* phytase or a mutant mature peptide thereof is as shown in SEQ ID NO. 14.

In another embodiment of the present invention, the codon-optimized DNA sequence encoding *Escherichia coli* phytase or a mutant mature peptide thereof is as shown in SEQ ID NO. 16.

In still another aspect, the present invention provides a method for enhancing the secretory expression of *Escherichia coli* phytase or a mutant thereof in a filamentous fungus. The method comprises linking the *Aspergillus oryzae* TAKA amylase signal peptide to a DNA sequence encoding *Escherichia coli* phytase or a mutant mature peptide thereof, and inserting an expression cassette comprising the sequence into a filamentous fungus for expression, where the nucleotide sequence of the *Aspergillus oryzae* TAKA amylase is as shown in SEQ ID NO. 12.

In one embodiment of the present invention, the amino acid sequence of the *Aspergillus oryzae* TAKA amylase is as shown in SEQ ID NO. 13.

In one embodiment of the present invention, the filamentous fungus is selected from *Aspergillus niger*.

In one embodiment of the invention, the *Escherichia coli* phytase has an amino acid sequence as shown in SEQ ID NO. 4, and the mutant of the *Escherichia coli* phytase has an amino acid sequence as shown in SEQ ID NO. 15 or SEQ ID NO. 17.

In one embodiment of the present invention, the DNA sequence encoding the *Escherichia coli* phytase or a mutant mature peptide thereof is not codon optimized.

In another embodiment of the present invention, the DNA sequence encoding *Escherichia coli* phytase or a mutant mature peptide thereof is codon optimized.

In another embodiment of the present invention, the codon-optimized DNA sequence encoding the *Escherichia coli* phytase or a mutant mature peptide thereof has a nucleotide sequence as shown in SEQ ID NO. 8; or has a nucleotide sequence that is at least 95%, 96%, 97%, 98% or 99% homologous to the nucleotide sequence as shown in SEQ ID NO. 8, and encodes a protein having the phytase activity.

In a preferred embodiment of the present invention, the codon-optimized DNA sequence encoding the *Escherichia coli* phytase or a mutant mature peptide thereof is as shown in SEQ ID NO. 14.

In a preferred embodiment of the present invention, the codon-optimized DNA sequence encoding the *Escherichia coli* phytase or a mutant mature peptide thereof is as shown in SEQ ID NO. 16.

An expression cassette, a recombinant expression vector, a recombinant strain, a transgenic cell line or a recombinant strain comprising the gene encoding the *Escherichia coli* phytase is also provided.

To construct an *Escherichia coli* phytase expression cassette, a specific promoter, terminator, signal peptide sequence, and regulatory sequence are required. e.g., 5' UTR, 3' UTR, and the like.

The promoter may be an endogenous promoter from *Aspergillus niger*, such as the glycosylase gene promoter, neutral amylase gene promoter, acid amylase gene promoter, and α-glucosidase gene promoter, etc. from *Aspergillus niger*; or an exogenous promoter, such as the neutral amylase gene promoter from *Aspergillus oryzae*, glycosylase gene promoter from *Rhizopus oryzae*; or a promoter variant, such as the *Aspergillus niger* neutral amylase gene promoter variant. In the present invention, the *Aspergillus niger* glycosylase gene promoter or *Aspergillus niger* neutral amylase gene promoter variant is preferred.

A regulatory sequence may be linked to the 3' end of the promoter, for example, a suitable leader sequence (5' UTR), that is, an untranslated region of mRNA important for the translation of the host cell, such as the leader sequence of *Aspergillus oryzae* neutral amylase and *Aspergillus nidulans* triose-phosphateisomerase;

For the secretory expression of a specific protein, a signal peptide sequence is required, and in the present invention, the *Aspergillus oryzae* TAKA amylase signal peptide is preferred for the *Escherichia coli* phytase.

Preferred terminators are obtained from the genes of *Aspergillus niger* glycosylase, *Aspergillus oryzae* TAKA amylase, *Aspergillus nidulans* anthranilate synthase, *Aspergillus niger* alpha-glucosidase and *Fusarium oxysporum* trypsin-like protease.

A specific gene is linked to the promoter, the regulatory sequence, the signal peptide sequence, and the terminator to form an expression cassette. It can be inserted into the genome of *Aspergillus niger* by conventional methods, and can be randomly inserted into the genome or integrated into one or more loci. Optional loci include gla (glycosylase), amya (neutral amylase), amyb (neutral amylase), aa (acid amylase), agda (alpha glucosidase), and agdb (alpha glucosidase).

The expression cassette can preferably be linked with one or more selectable markers, which allow(s) for simple selection of cells or strains that have been transformed, transfected, and transduced. The selectable marker is a gene whose product provides biocidal or viral resistance, resistance to heavy metals, prototrophy to auxotrophs, and the like. Selectable markers for filamentous fungal host cells include, but are not limited to, amdS (acetamidase), argB (ornithine carbamoyltransferase), bar (phosphinothricin acetyltransferase), hyg (hygromycin phosphofransferose), niaD (nitrate reductase), pyrG (orotidine-5'-phosphate decarboxylase), sC (sulphate adenylyltransferase) and trpC (anthranilate synthase) and their equivalents. Preferred for use in *Aspergillus* cells are amdS and hyg of *Aspergillus nidulans* or *Aspergillus oryzae*.

The expression cassette is preferably linked to one or more counter-selectable markers (negative selection markers). Selectable markers for filamentous fungal host cells include, but are not limited to, amdS (acetamidase), pyrG (orotidine-5'-phosphate decarboxylase), and hsvTK (herpes simplex virus thymidine kinase).

A recombinant expression vector is obtained by inserting the *Escherichia coli* phytase gene or an expression cassette containing the gene into an expression vector.

A recombinant strain is obtained by introducing the recombinant expression vector into a host strain of interest which is preferably *Aspergillus niger*.

Use of the *Escherichia coli* phytase gene in increasing the expression level of *Escherichia coli* phytase is provided.

Use of the expression cassette, the recombinant expression vector, and the recombinant strain in increasing the expression level of *Escherichia coli* phytase is also provided.

A method for producing *Escherichia coli* phytase is provided, which comprises fermenting and culturing the transgenic recombinant strain to obtain *Escherichia coli* phytase.

The method for introducing a DNA fragment into *Aspergillus niger* in the present invention is a conventional method in the art.

Codon optimization refers to the redesign of genes by using preferred codons instead of low-utilization or rare codons. For a detailed description of codon optimization, see the article of Joshua B. Plotkin and Grzegorz Kudla (Nat Rev Genet. 2011; 12(1): 32-42.). Codon optimization has been widely used in heterologous expression systems.

Beneficial Effects of the Present Invention:

The present inventors have found that for the gene encoding *Escherichia coli* phytase or a mutant thereof, it is preferred to synthesize an artificial gene after codon optimization, and after being linked with the *Aspergillus oryzae* TAKA amylase signal peptide, the constructed expression cassette is introduced into *Aspergillus niger* for expression. In this way, a large amount of secreted and expressed phytase can be obtained in the culture supernatant.

DETAILED DESCRIPTION

Example 1

Construction of pHphtk Plasmid

Figure 1:
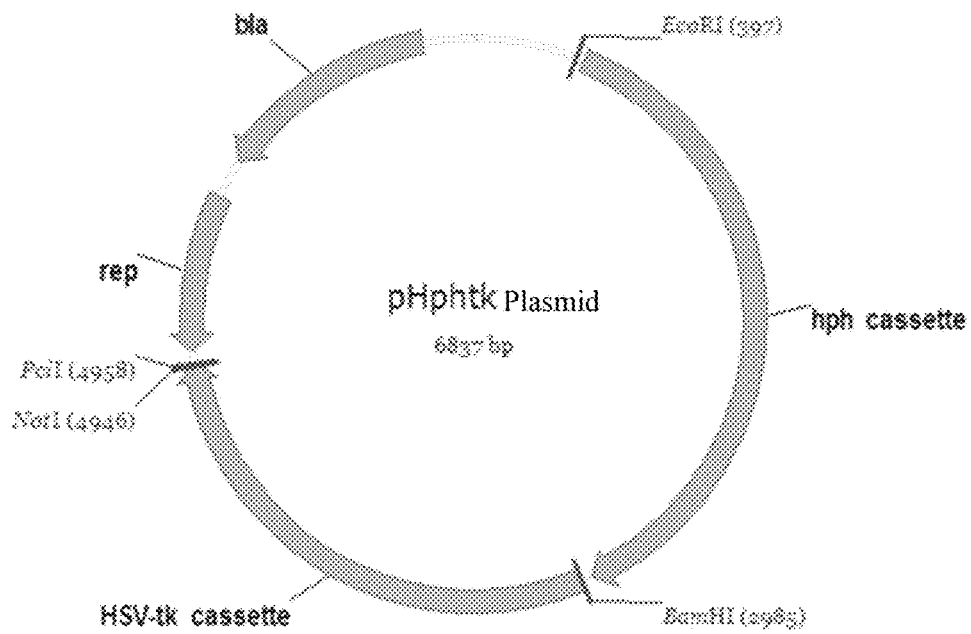
FIG. 1 is mapping of a pHphtk plasmid.

The plasmid contains the following three parts, and is constructed by Nanjing Kingsray Biotechnology Co., Ltd., and the mapping of the plasmid is shown in FIG. 1.
(1) a 2305 bp fragment obtained by XbaI-PciI double digestion of pUC57 plasmid;
(2) a hph gene expression cassette, having a sequence as shown in SEQ ID NO. 18; and
(3) an HSV-tk expression cassette, having a sequence as shown in SEQ ID NO. 19.

Example 2

Figure 2:
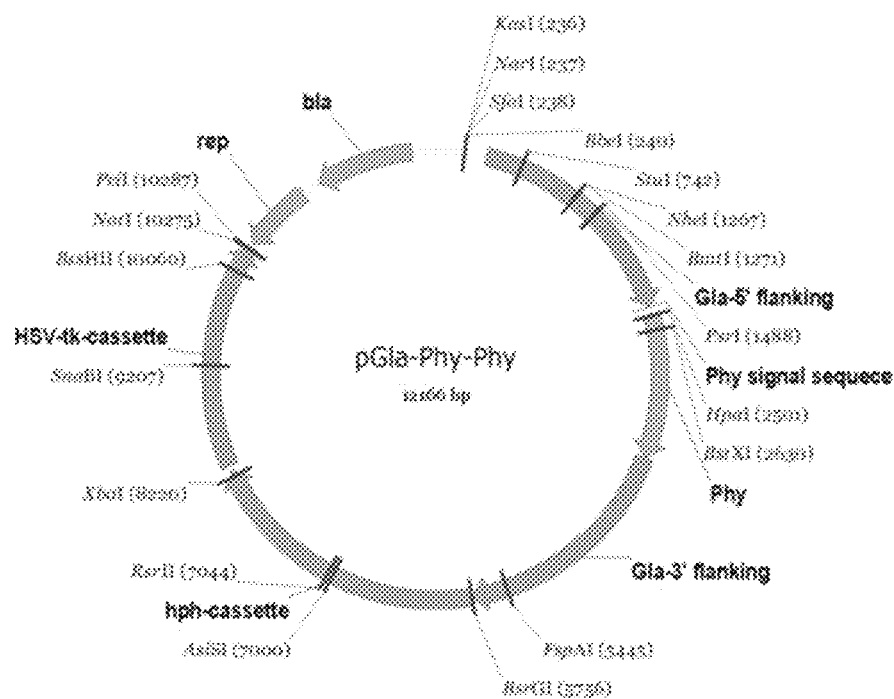
FIG. 2 is mapping of a pGla-Phy-Phy plasmid.
Figure 3:
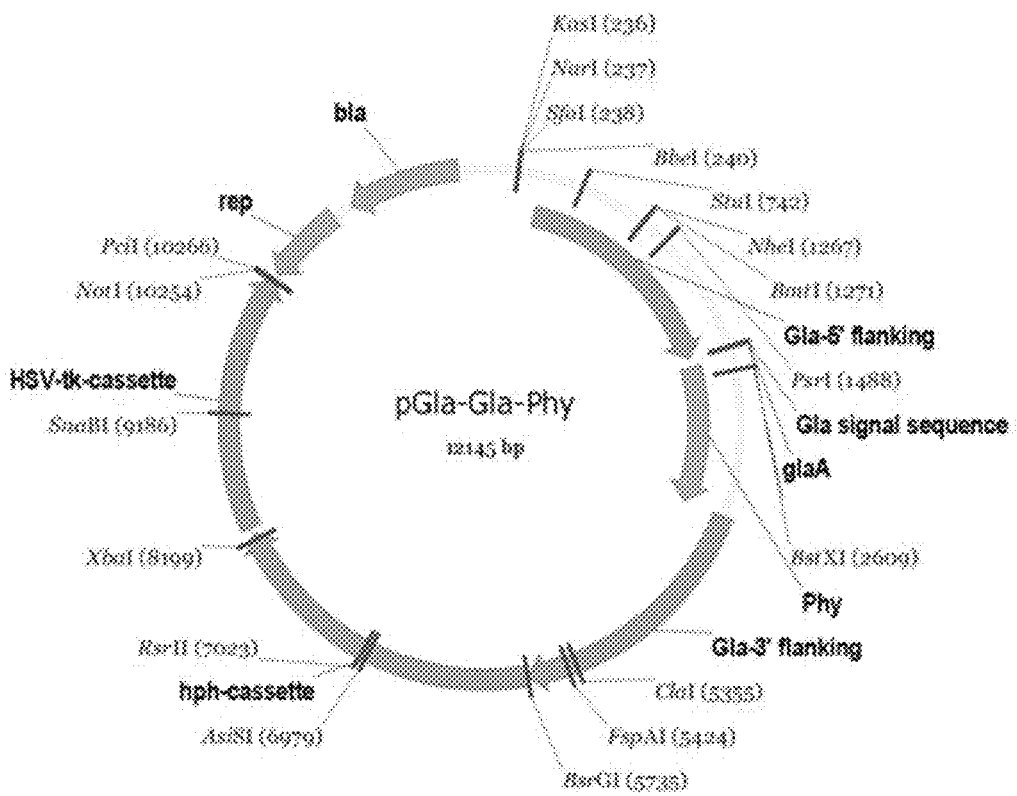
FIG. 3 is mapping of a pGla-Gla-Phy plasmid.
Figure 4:
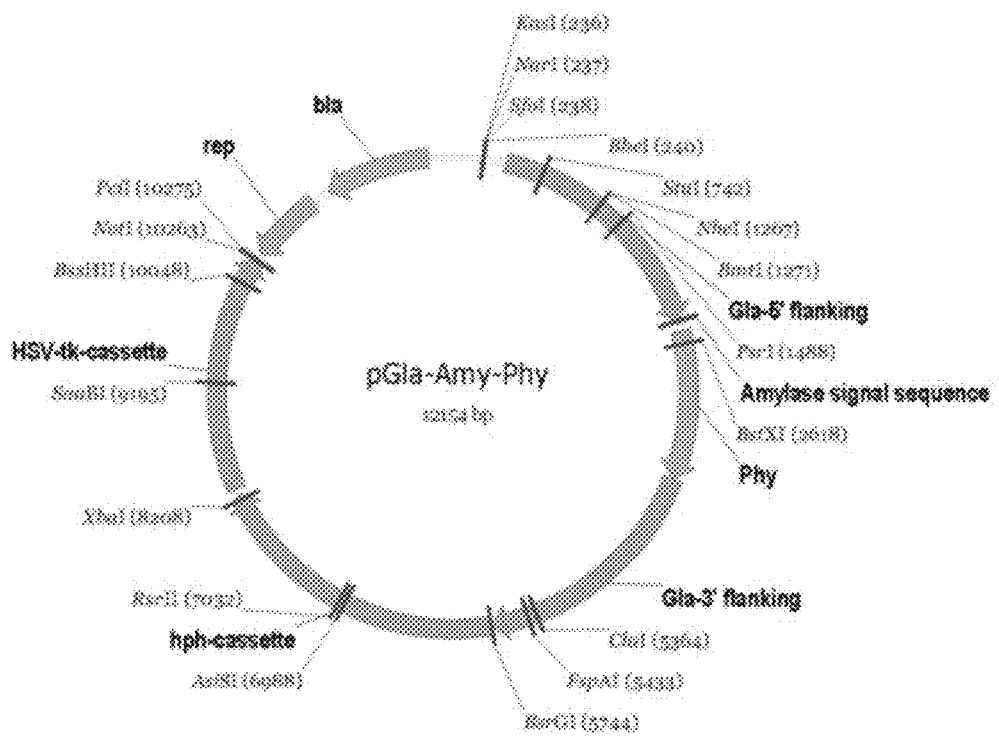
FIG. 4 is mapping of a pGla-Amy-Phy plasmid.

Construction of Plasmid Integrated with *Escherichia coli* Phytase Guided by Various Signal Peptides An *Escherichia coli* phytase expression cassette was integrated into the *Aspergillus niger* glycosylase locus for expression, where the glycosylase promoter and the glycosylase terminator were used. pGla-Phy-Phy, pGla-Gla-Phy, and pGla-Amy-Phy plasmids were constructed respectively. Various signal peptide sequences including the *Escherichia coli* phytase signal peptide (SEQ ID NO. 5), *Aspergillus niger* glycosylase signal peptide (SEQ ID NO. 10), and *Aspergillus oryzae* TAKA amylase signal peptide (SEQ ID NO. 12) were respectively linked to the wide-type *Escherichia coli* phytase mature peptide encoding DNA sequence Phy (SEQ ID NO. 3), and then used to replace the *Aspergillus niger* glycosylase gene. The phytase mature peptide encoding DNA sequence Phy (SEQ ID NO. 3) derived from *Escherichia coli* ATCC 8739 was synthesized by Nanjing Kingsray Biotech Co., Ltd., the Phy signal peptide DNA sequence was synthesized by Nanjing Kingsray Biotech Co., Ltd., the *Aspergillus niger* glycosylase signal peptide (SEQ ID NO. 10) and the *Aspergillus oryzae* TAKA amylase signal peptide (SEQ ID NO. 12) were introduced onto the Phy sequence by PCR using primers. The integrated plasmid was constructed as follows. The pHphtk plasmid was linearized by vector-F and vector-R primers. The genome of *Aspergillus niger* (from China Center of Industrial Culture Collection under Accession No. CICC2462) was used as a template, and the Gla-5'-F and Gla-5'-R and the Gla-3'-F and Gla-3'-R were respectively used to amplify the 5' and 3' flanking sequences of the glycosylase gene, where each fragment was 2000 bp long. The wild-type *Escherichia coli* phytase sequence Phy (SEQ ID NO. 1) was amplified using Phy-Phy-F and Phy-Phy-R. The linearized pHphtk vector, the 5' and 3' flanking fragments of the glycosylase gene, and the Phy fragment were recombined by Gibson Assembly® Master Mix Kit (E2611, New England Biolabs) to obtain an integrated plasmid pGla-PepWT, the sequence of which was confirmed by sequencing. Mapping of the plasmid is shown in FIG. 2. Gla-Phy-F and Phy-Phy-R were used as primers, and the Phy fragment (SEQ ID NO. 1) was used as a template to obtain a Gla-Phy fragment by PCR amplification. In this fragment, the *Aspergillus niger* glycosylase signal peptide sequence was introduced. The linearized pHphtk vector, the 5' and 3' flanking fragments of the glycosylase gene, and the Gla-Phy fragment were recombined by Gibson Assembly® Master Mix Kit to obtain an integrated plasmid pGla-Gla-Phy, the sequence of which was confirmed by sequencing. Mapping of the plasmid is shown in FIG. 3. Amylase-Phy-F and Phy-Phy-R were used as primers and the Phy fragment (SEQ ID NO. 1) was used as a template to obtain an Amylase-Phy fragment by PCR amplification. In this fragment, the *Aspergillus oryzae* TAKA amylase signal peptide sequence was introduced. The linearized pHphtk vector, the 5' and 3' flanking fragments of the glycosylase gene, and the Amylase-Phy fragment were recombined by Gibson Assembly® Master Mix Kit to obtain an integrated plasmid pGla-Amy-Phy, the sequence of which was confirmed by sequencing. Mapping of the plasmid is shown in FIG. 4. The 2 kb 5'-terminal flanking DNA sequence of the glycosylase gene is shown in SEQ ID NO. 20, and the 2 kb 3'-terminal flanking DNA sequence is shown in SEQ ID NO. 21. Phy-Phy, Gla-Phy and Amy-Phy are as shown in SEQ ID NO. 22, SEQ ID NO. 23 and SEQ ID NO. 24, respectively.

Related primer sequences are listed below:

| Primer name | Sequence (5'→3') |
|---|---|
| vector-F | gtacagtgaccggtgactctttctggcatg (SEQ ID NO: 30) |
| vector-R | gatgcattcgcgaggtaccgagctc (SEQ ID NO: 31) |
| Gla-5'-F | aattcgagctcggtacctcgcgaatgcatcctacca atgctctcgaggattgcctgaacattgacattcggc (SEQ ID NO: 32) |
| Gla-5'-R | tgctgaggtgtaatgatgctggg (SEQ ID NO: 33) |
| Gla-3'-F | acaatcaatccatttcgctatagttaaaggatg (SEQ ID NO: 34) |
| Gla-3'-R | catgccagaaagagtcaccggtcactgtacatggc caatgtggtagccgttatcag (SEQ ID NO: 35) |
| Phy-Phy-F | cttcatccccagcatcattacacctcagcaatgtc agatatgaaaagcggaaacatatc (SEQ ID NO: 36) |
| Phy-Phy-R | cattaactatagcgaaatggattgattgtttacaa actgcacgccggtatgc (SEQ ID NO: 37) |
| Gla-Phy-F | cttcatccccagcatcattacacctcagcaatgtc gttccgatctctactcgccctgagcggcctcgtct gcacagggttggcaaatgtgatttccaagcgcgcg cagagtgagccggagctgaagct (SEQ ID NO: 38) |
| Amylase-Phy-F | cttcatccccagcatcattacacctcagcaatggt cgcctggtggtccctcttcctctacggtctccagg tcgccgccccgccctcgccgccaccccgccgac tggcgctcccagagtgagccggagctgaagct (SEQ ID NO: 39) |

Example 3

Construction of Codon-Optimized *Escherichia coli* Phytase Integrated Plasmid

Figure 5:
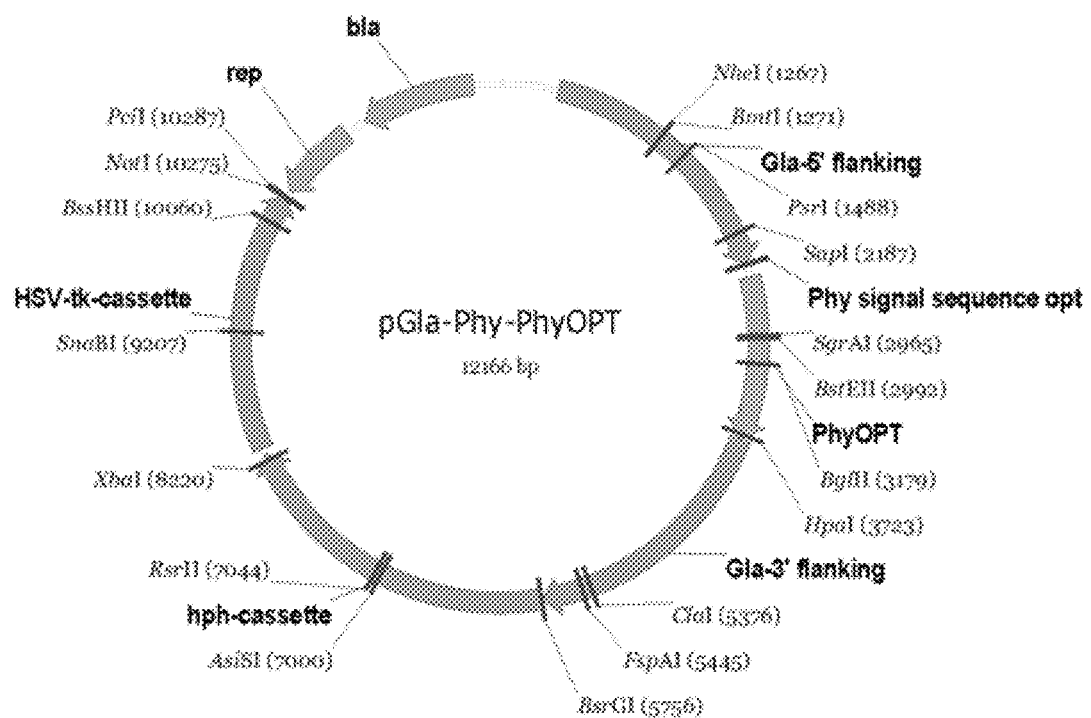
FIG. 5 is mapping of a pGla-Phy-PhyOPT plasmid.
Figure 6:
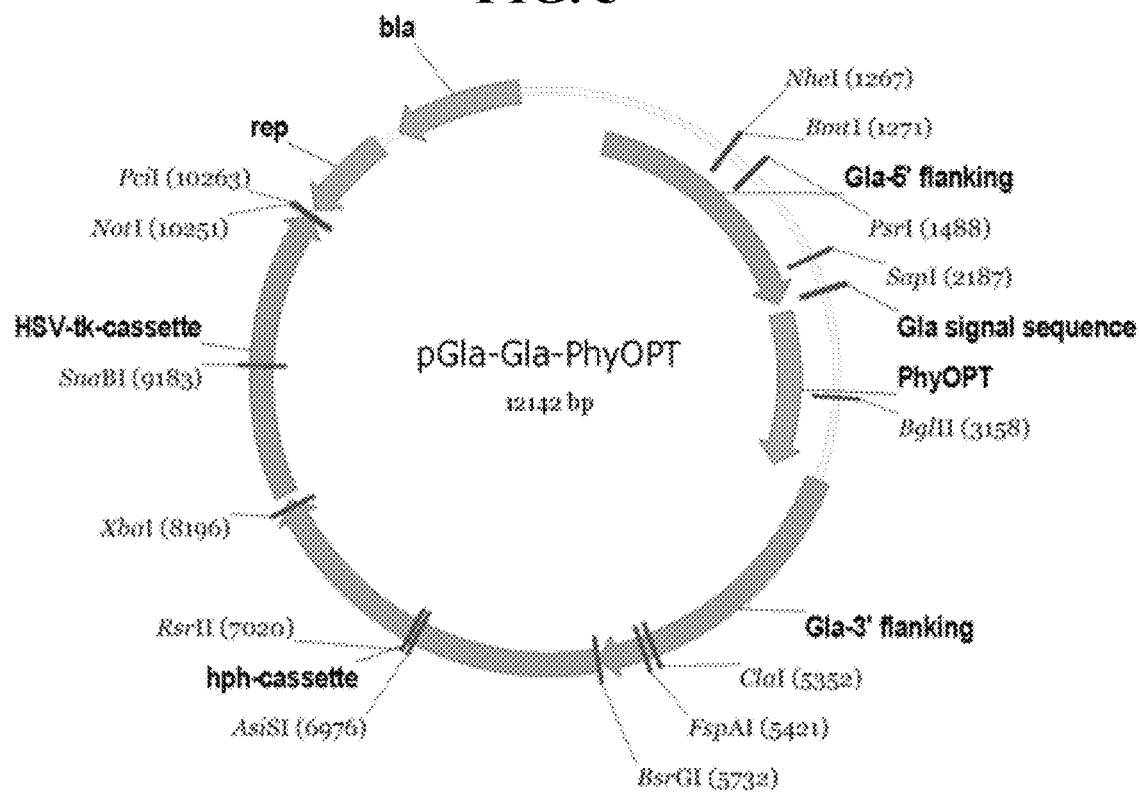
FIG. 6 is mapping of a pGla-Gla-PhyOPT plasmid.
Figure 7:
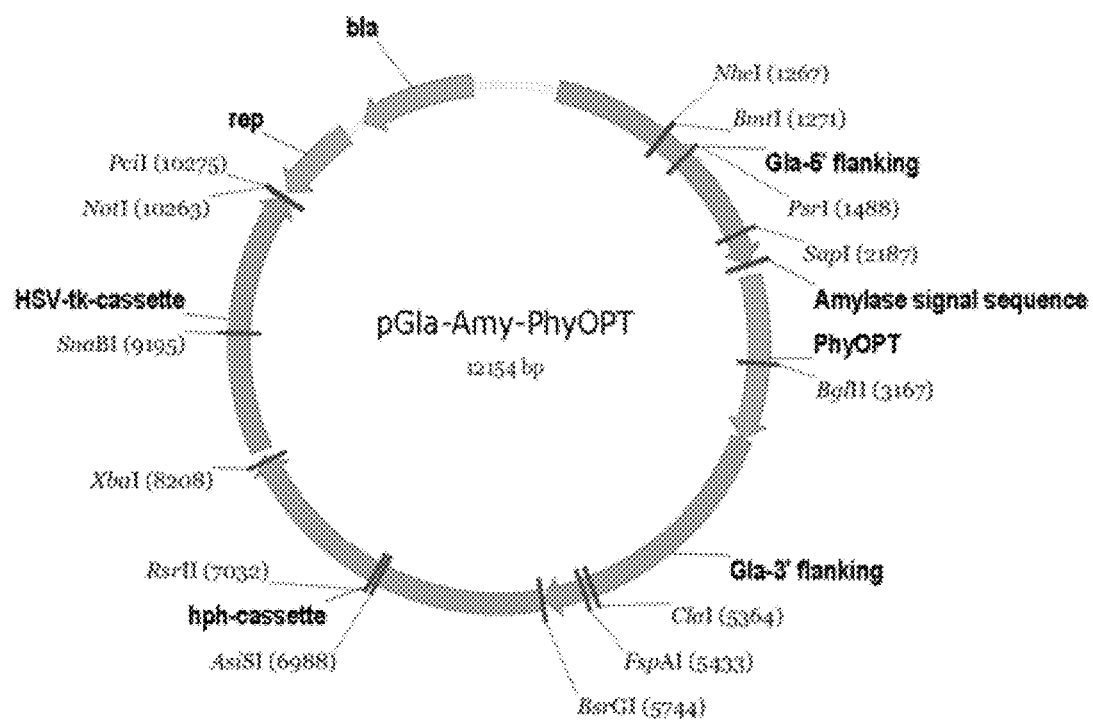
FIG. 7 is mapping of a pGla-Amy-PhyOPT plasmid.

Plasmids pGla-Phy-PhyOPT, pGla-Gla-PhyOPT, and pGla-Amy-PhyOPT were constructed respectively. Various signal peptide sequences including the *Escherichia coli* phytase signal peptide, *Aspergillus niger* glycosylase signal peptide, and *Aspergillus oryzae* TAKA amylase signal peptide were respectively linked to the codon-optimized *Escherichia coli* phytase sequence PhyOPT (SEQ ID NO. 8), and then used to replace the *Aspergillus niger* glycosylase gene. The phytase sequence derived from *Escherichia coli* ATCC 8739 was codon optimized to have a sequence as shown in SEQ ID NO. 8, which was synthesized by Nanjing Kingsray Biotechnology Co., Ltd. Similarly, the Phy signal peptide was optimized to have a sequence as shown in SEQ ID NO. 9. The integrated plasmid was constructed as follows. The pHphtk plasmid was linearized by vector-F and vector-R primers. The genome of *Aspergillus niger* (available from China Center of Industrial Culture Collection under Accession No. CICC2462) eras used as a template, and the Gla-5'-F and Gla-5'-R and the Gla-3'-F and Gla-3'-R were respectively used to amplify the 5' and 3' flanking sequences of the glycosylase gene, where each fragment was 2000 bp long. Optimized *Escherichia coli* phytase sequence PhyOPT was amplified using Phy-PhyOPT-F and Phy-PhyOPT-R, in which optimized Phy signal peptide sequence was introduced on the primer. The linearized pHphtk vector, the 5' and 3' flanking fragments of the glycosylase gene, and the Phy fragment were recombined by Gibson Assembly® Master Mix Kit (E2611 New England Biolabs) to obtain an integrated plasmid pGla-Phy-PhyOPT, the sequence of which was confirmed by sequencing. Mapping of the plasmid is shown in FIG. 5. Gla-PhyOPT-F and Phy-PhyOPT-R were used as primers, and the PhyOPT fragment was used as a template to obtain a Gla-PhyOPT fragment by PCR amplification. In this fragment, the *Aspergillus niger* glycosylase signal peptide sequence was introduced. The linearized pHphtk vector, the 5' and 3' flanking fragments of the glycosylase gene, and the Gla-PhyOPT fragment were recombined by Gibson Assembly® Master Mix Kit to obtain an integrated plasmid pGla-Gla-Phy, the sequence of which was confirmed by sequencing. Mapping of the plasmid is shown in FIG. 6. Amylase-PhyOPT-F and Phy-PhyOPT-R were used as primers and the PhyOPT fragment was used as a template to obtain an Amylase-PhyOPT fragment by PCR amplification. In this fragment, the *Aspergillus oryzae* TAKA amylase signal peptide sequence was introduced. The linearized pHphtk vector, the 5' and 3' flanking fragments of the glycosylase gene, and the Amylase-PhyOPT fragment were recombined by Gibson Assembly® Master Mix Kit to obtain an integrated plasmid pGla-Amylase-PhyOPT, the sequence of which was confirmed by sequencing. Mapping of the plasmid is shown in FIG. 7. The 2 kb 5'-terminal flanking DNA sequence of the glycosylase gene is shown in SEQ ID NO. 20, and the 2 kb 3'-terminal flanking DNA sequence is shown in SEQ ID NO. 21. The sequences of the Phy-PhyOPT, Gla-PhyOPT, and Amy-PhyOPT expression cassettes are respectively as shown in SEQ ID NO. 25, SEQ ID NO. 26, and SEQ ID NO. 27.

Related primer sequences are listed below:

| Primer name | Sequence (5'→3') |
|---|---|
| vector-F | Gtacagtgaccggtgactctactggcatg (SEQ ID NO: 30) |
| vector-R | gatgcattcgcgaggtaccgagctc (SEQ ID NO: 31) |
| Gla-5'-F | aattcgagctcggtacctcgcgaatgcatcctacca atgctctcgaggattgcctgaacattgacattcggc (SEQ ID NO: 32) |
| Gla-5'-R | tgctgaggtgtaatgatgctggg (SEQ ID NO: 33) |

-continued

| Primer name | Sequence (5'→3') |
|---|---|
| Gla-3'-F | acaatcaatccatttcgctatagttaaaggatg (SEQ ID NO: 34) |
| Gla-3'-R | catgccagaaagagtcaccggtcactgtacatggcc aatgtggtagccgttatcag (SEQ ID NO: 35) |
| Phy-PhyOPT-F | cttcatccccagcatcattacacctcagcaatgtcc gacatgaagtccggtaacatctccatgaaggccatc ctgatcccttcctgtccctgctgatcccctgacc ccccagtccgccttcgcccagtccgaacccgagctg aagc (SEQ ID NO: 40) |
| Phy-PhyOPT-R | cctttaactatagcgaaatggattgattgtttagag ggagcaggcggggatgc (SEQ ID NO: 41) |
| Gla-PhyOPT-F | cacatccccagcatcattacacctcagcaatgtcga ccgatctctactcgccctgagcggcctcgtctgcac agggaggcaaatgtgataccaagcgcgcgcagtccg agcccgagctcaagc (SEQ ID NO: 42) |
| Amylase-Phy-OPT-F | cttcatccccagcatcattacacctcagcaatggtc gcctggtggtccctcttcctctacggtctccagatc gccgccccgccctcgccgccaccccgccgactgg cgacccagtccgagcccgagctcaagc (SEQ ID NO: 43) |

Example 4

Figure 8:
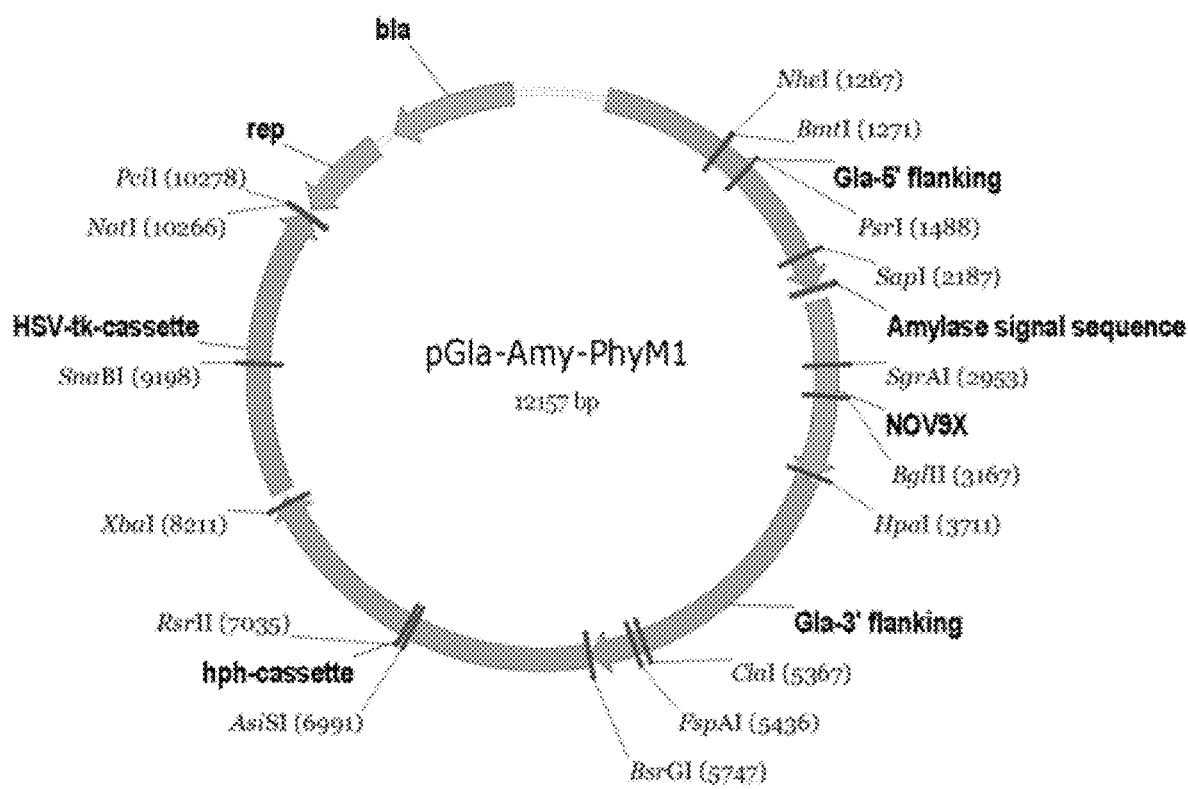
FIG. 8 is mapping of a pGla-Amy-PhyM1 plasmid.
Figure 9:
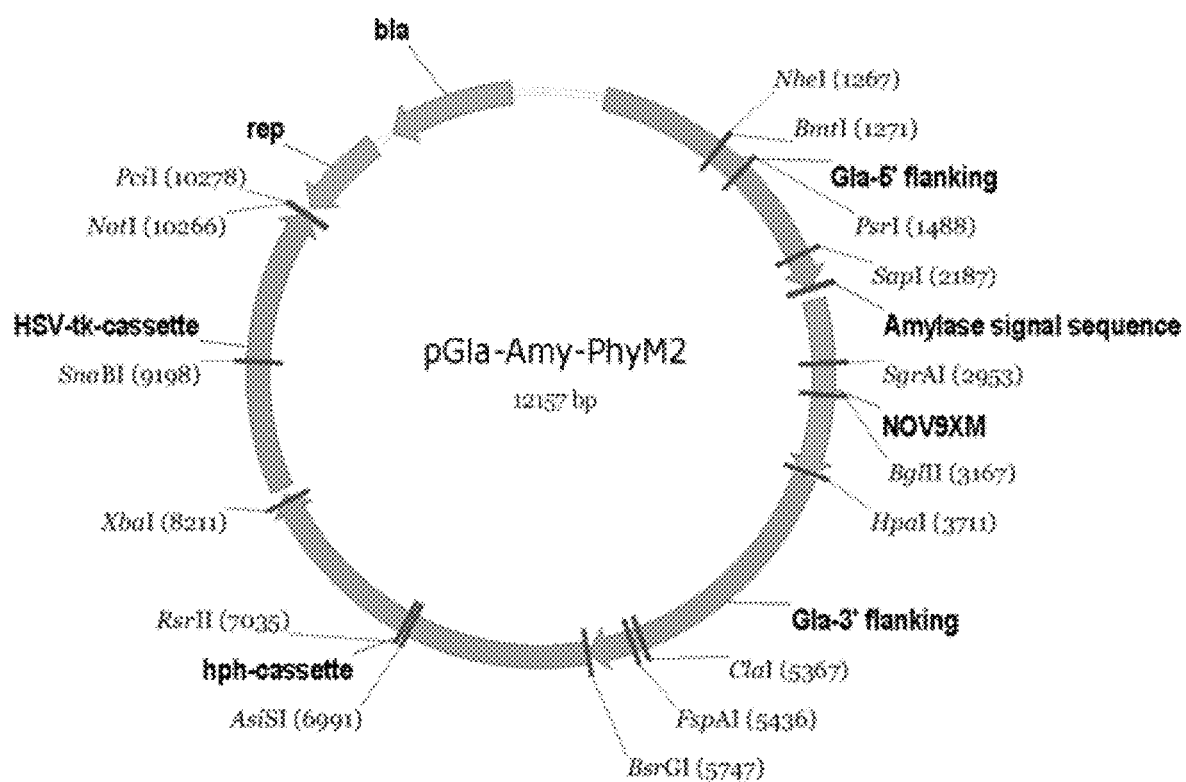
FIG. 9 is mapping of a pGla-Amy-PhyM2 plasmid.

Construction of Codon-Optimized *Escherichia coli* Phytase Mutant Integrated Plasmid U.S. Pat. No. 7,432,098 describes the *Escherichia coli* phytase mutant NOV9X, which has better heat resistance and is more suitable for use in the area of feed. NOV9X has 9 amino acid mutations compared to the *Escherichia coli* phytase in the present invention. In order to verify whether NOV9X can be efficiently expressed under the guidance of *Aspergillus oryzae* TAKA amylase signal, 17 base mutations were introduced to PhyOPT to obtain the DNA sequence of NOV9X, as shown in SEQ ID NO. 14. NOV9X has 98.6% sequence identity to the codon optimized *Escherichia coli* phytase mature peptide DNA sequence (SEQ ID NO. 8). NOV9X is synthesized by Nanjing Kingsray Biotechnology Co., Ltd., and the mature peptide sequence encoded thereby is shown in SEQ ID NO. 15. 43 base mutations were further introduced in NOV9X to form NOV9XM, as shown in SEQ ID NO. 16, which has 95.9% sequence identity to the codon-optimized *Escherichia coli* phytase mature peptide coding DNA sequence (SEQ ID NO. 8). NOV9X is synthesized by Nanjing Kingsray Biotechnology Co., Ltd., and the mature peptide sequence encoded thereby is shown in SEQ ID NO. 17. Plasmids pGla-Amy-PhyM1 and pGla-Amy-PhyM2 were constructed to integrate Amy-NOV9X and Amy-NOV9XM into *Aspergillus niger* glycosylase locus, respectively. The integrated plasmid was constructed as follows. The pHphtk plasmid was linearized by vector-F and vector-R primers. The genome of *Aspergillus niger* (from China Center of Industrial Culture Collection under Accession No. CICC2462) was used as a template, and the Gla-5'-F and Gla-5'-R and the Gla-3'-F and Gla-3'-R were respectively used to amplify the 5' and 3' flanking sequences of the glycosylase gene, where each fragment was 2000 bp long. Amylase-PhyOPT-F and Phy-PhyOPT-R were used as primers and the NOV9X and NOV9XM fragments were respectively used as a template to obtain Amylase-PhyM1 and Amylase-PhyM2 fragments by PCR amplification. In the two fragments, the *Aspergillus oryzae* TAKA amylase signal peptide sequence was introduced. The linearized pHphtk vector, the 5' and 3' flanking fragments of the glycosylase gene, and the Amylase-PhyM1 fragment were recombined by Gibson Assembly® Master Mix Kit to obtain an integrated plasmid pGla-Amylase-PhyM1, the sequence of which was confirmed by sequencing. Mapping of the plasmid is shown in FIG. 8. The linearized pHphtk vector, the 5' and 3' flanking fragments of the glycosylase gene, and the Amylase-PhyM2 fragment were recombined by Gibson Assembly® Master Mix Kit to obtain an integrated plasmid pGla-Amylase-PhyM2, the sequence of which was confirmed by sequencing. Mapping of the plasmid is shown in FIG. 9. The 2 kb 5'-terminal flanking DNA sequence of the glycosylase gene is shown in SEQ ID NO. 20, and the 2 kb 3'-terminal flanking DNA sequence is shown in SEQ ID NO. 21. The Amy-PhyM1 and Amy-PhyM2 expression cassettes are respectively as shown in SEQ ID NO. 28 and SEQ ID NO. 29.

Related primer sequences are listed below:

| Primer name | Sequence (5'→3') |
|---|---|
| vector-F | gtacagtgaccgatgactctttctggcatg (SEQ ID NO: 30) |
| vector-R | gatgcattcgcgaggtaccgagctc (SEQ ID NO: 31) |
| Gla-5'-F | aattcgagctcggtacctcgcgaatgcatcct accaatgctctcgaggattgcctgaacattga cattcggc (SEQ ID NO: 32) |
| Gla-5'-R | tgctgaggtgtaatgatgctggg (SEQ ID NO: 33) |
| Gla-3'-F | acaatcaatccatttcgctatagttaaaggat g (SEQ ID NO: 34) |
| Gla-3'-R | catgccagaaagagtcaccggtcactgtacat ggccaatgtggtagccgttatcag (SEQ ID NO: 35) |
| Amylase-PhyOPT-F | Cttcatccccagcatcattacacctcagcaa tggtcgcctggtggtccctcttcctctacgc cgagcccgagctcaagc (SEQ ID NO: 43) |
| Phy-PhyOPT-R | cctttaactatagcgaaatggattgattgttt acagggagcaggcggggatgc (SEQ ID NO: 44) |

Example 5

Integration of Each Expression Cassette into *Aspergillus niger*

The starting strain in this Example was AND4L, which was obtained by knocking out the glycosylase gene, the fungal amylase gene and the acid amylase gene from the CICC2462 strain. The *Aspergillus niger* gene knockout/knockin method could be implemented by referring to the technical method disclosed in the examples in CN 103937766A or CN 104962594A. The integration of Phy-PhyOPT and PhyM into the glycosylasee locus in this example was achieved in the same manner as that in the example of CN 104962594A, i.e., by the method described by Delmas et al. (Appl Environ Microbiol. 2014, 80(11): 3484-7). Specifically, a circular DNA vector is used, comprising gla 5' and 3' flanking sequences, a selectable marker, a reverse selectable marker (or a negative selectable marker), and an *Escherichia coli* replication sequence, i.e. the plasmid as described in Examples 1 to 4. The circular vector was transferred into *Aspergillus niger*, and the recombinant strain was obtained by forward selection, and the knockout/knock-in strain was obtained by the reverse selectable marker.

Protoplast transformation was used to introduce pGla-Phy-Phy, pGla-Gla-Phy, pGla-Amy-Phy, pGla-Phy-PhyOPT, pGla-Gla-PhyOPT, pGla-Amy-PhyOPT, pGla-Amy-PhyM1 and pGla-Amy-PhyM2 separately. The specific steps were as follows.

Preparation of protoplasts: *Aspergillus niger* mycelium was cultured in a TZ liquid medium with rich nutrients (containing 0.8% of beef extract powder; 0.2% of yeast extract; 0.5% of peptone; 0.2% of NaCl; and 3% of sucrose; pH 5.8). The mycelium was filtered from the liquid culture by mira-cloth (Calbiochem) and washed with 0.7 M NaCl (pH 5.8). The mycelium was drained and transferred to an enzymatic hydrolyzing buffer (pH 5.8) containing 1% of cellulase (Sigma), 1% of helicase (Sigma) and 0.2% of lywallzyme (Sigma), and enzymatically hydrolyzed at 30° C. and 65 rpm for 3 hrs. Then, the enzymatic hydrolyzing buffer containing the protoplast was placed on ice and filtered through four layers of lens paper. The obtained filtrate was mildly centrifuged at 3000 rpm for 10 minutes at 4° C., and the supernatant was discarded. The protoplast attached to the tube wall was washed once with an STC buffer (containing 1 M D-Sorbitol, 50 mM $CaCl_2$, 10 mM Tris, pH 7.5), and finally resuspended in an appropriate amount of the STC buffer.

10 µl (concentration: 100 ng/µl) of the circular plasmids pGla-Phy-Phy, pGla-Gla-Phy, pGla-Amy-Phy, pGla-Phy-PhyOPT, pGla-Gla-PhyOPT, pGla-Amy-PhyOPT, pGla-Amy-PhyM 1 and pGla-Amy-PhyM2 were respectively added to 100 µl of the protoplast suspension, mixed until uniform, and then stood for 25 min at room temperature. Then a total of 900 µl of a PEG solution was added in 3 times, mixed until uniform and allowed to stand for 25 min at room temperature. The solution was centrifuged at room temperature for 10 min at 3000 rpm. The supernatant was discarded and the protoplast attached to the wall of the tube was resuspended in 1 ml of the STC buffer. The suspension was mixed with a TB3 medium (containing 0.3% of yeast extract, 0.3% of acidically hydrolyzed casein, 20% of sucrose, and 0.7% of agar) previously cooled to about 45° C. and plated. After solidification, the plate was placed and cultured in an incubator at 34° C. After 24 hrs, a layer of TB3 solid medium (containing 1% of agar, the remaining components being the same as above) containing 300 ng/µl of hygromycin was further plated on the plate, and the plate was further incubated in an incubator at 34° C. for 4-5 days. The transformants that grew out of the upper medium were the integrated transformants. Several integrated transformants were randomly picked and passaged respectively on TB3 solid medium containing 300 ng/µl hygromycin. After incubation at a constant temperature of 34° C. for 3 days, the mycelium was collected, frozen in liquid nitrogen, and then ground. Subsequently, the genomic DNA of the integrated transformant was extracted with a fungal genome extraction kit (Hangzhou Bori Technology Co., Ltd.). Finally, the genomic DNA of the integrated transformant was identified by PCR, in which the primers for identification were Pep-5test-F and Pep-5test-R, and Pep-3test-F and Pep-3test-R. The PCR product was sequenced and confirmed to be integrated into glycosylase locus.

Related primer sequences are listed below:

| Primer name | Sequence (5'→3') |
|---|---|
| Phy-5test-F | aatcgtgtccgcagatgtacttcac (SEQ ID NO: 45) |
| Phy-5test-R | ataatcatccactgcacctcagagc (SEQ ID NO: 46) |
| Phy-3test-F | tttcccagtcacgacgttgtaaaac (SEQ ID NO: 47) |
| Phy-3test-R | aactcgaacagtgtaggtgcaatgtc (SEQ ID NO: 48) |

A suitable amount of the ground mycelium of the confirmed positive transformant was picked up into a centrifuge tube containing 1 ml of sterile water, and vortexed to form a mycelium suspension. 100 µl was taken and coated onto a TB3 solid plate containing 10 µM 5-F2dU (5-fluoro-2-deoxyuridine, manufacturer: Sigma), and incubated at a constant temperature of 34° C. for 4-5 days. Knockout transformants were grown. The transformant should be unable to grow on 300 ng/µl hygromycin-containing plates after two generations on 10 µM 5-F2dU plates (to prevent impure transformants). Then the genomic DNA of the knockout transformant was identified by PCR, in which the primer sequences and the genome extraction method were the same as above. PCR identification using Pep-5test-F and Pep-3test-R showed that the positive transformant product is 5.5 kb and the negative transformant is 6.3 kb. The positive transformants were confirmed by sequencing the PCR products to obtain strains AND4L-Phy-Phy, AND4L-Gla-Phy, AND4L-Amy-Phy, AND4L-Phy-PhyOPT, AND4L-Gla-PhyOPT, AND4L-Amy-PhyOPT, AND4L-Amy-PhyM1 and AND4L-Amy-PhyM2.

Example 6

Shake Flask Fermentation of Strains

The strains AND4L-Phy-Phy, AND4L-Gla-Phy, AND4L-Amy-Phy, AND4L-Phy-PhyOPT, AND4L-Gla-PhyOPT, AND4L-Amy-PhyOPT, AND4L-Amy-PhyM1 and AND4L-Amy-PhyM2 obtained in Example 5 were inoculated into a shake flask containing 50 ml of YPG medium (containing 2 g/L yeast extract, 2 g/L peptone, and 10% glucose) respectively, and cultured at 34° C. and 220 rpm for six days. The supernatant was subjected to denaturing, polyacrylamide gel electrophoresis (SDS-PAGE). For the expression of each strain, see Table 1 for details.

TABLE 1

Expression of strains

| Strain | Signal peptide | Whether the sequence is optimized | Expression |
| --- | --- | --- | --- |
| AND4L-Phy-Phy | *Escherichia coli* phytase | Not optimized | No expression |
| AND4L-Gla-Phy | *Aspergillus niger* glycosylase | Not optimized | No expression |
| AND4L-Amy-Phy | *Aspergillus oryzae* TAKA amylase | Not optimized | Low expression |
| AND4L-Phy-PhyOPT | *Escherichia coli* phytase | Optimized | No expression |
| AND4L-Gla-PhyOPT | *Aspergillus niger* glycosylase | Optimized | No expression |
| AND4L-Amy-PhyOPT | *Aspergillus oryzae* TAKA amylase | Optimized | High expression |
| AND4L-Amy-PhyM1 | *Aspergillus oryzae* TAKA amylase | Optimized | High expression |
| AND4L-Amy-PhyM2 | *Aspergillus oryzae* TAKA amylase | Optimized | High expression |

As can be seen from Table 1, after the DNA encoding *Escherichia coli* phytase or a mutant thereof is codon optimized, the expression level in the supernatant is good under the guidance of *Aspergillus oryzae* TAKA amylase signal peptide, and no protein expression occurs in the presence of other signal peptide sequences. For the non-optimized sequence, the expression level is also very low under the guidance of *Aspergillus oryzae* TAKA amylase signal peptide, which proves that the optimization of the DNA sequence is also critical for the expression. Good expression can also be achieved after 17 and 50 mutations were introduced into the optimized sequence, respectively.

The invention claimed is:

1. A signal peptide for enhancing the secretory expression of *Escherichia coli* phytase in a filamentous fungus, wherein the signal peptide is derived from *Aspergillus oryzae* TAKA amylase and has the amino acid sequence as shown in SEQ ID NO: 13, wherein the signal peptide is in a fusion protein with an *Escherichia coli* phytase having the amino acid sequence as shown in SEQ ID NO: 4, and wherein the filamentous fungus is *Aspergillus niger*.

2. The signal peptide for enhancing the secretory expression of *Escherichia coli* phytase in a filamentous fungus according to claim 1, wherein the signal peptide is encoded by the nucleotide sequence as shown in SEQ ID NO: 12.

3. A signal peptide for enhancing the secretory expression of *Escherichia coli* phytase or a mutant thereof in a filamentous fungus, wherein the signal peptide is derived from *Aspergillus oryzae* TAKA amylase and has the amino acid sequence as shown in SEQ ID NO:13, wherein the signal peptide is in a fusion protein with an *Escherichia coli* phytase mutant, wherein the mutant of the *Escherichia coli* phytase has the amino acid sequence as shown in or SEQ ID NO: 17, and wherein the filamentous fungus is *Aspergillus niger*.

4. The signal peptide for enhancing the secretory expression of *Escherichia coli* phytase in a filamentous fungus according to claim 1, wherein the *Escherichia coli* phytase is encoded by the nucleotide sequence as shown in SEQ ID NO: 7; or a nucleotide sequence that is at least 95%, 96%, 97%, 98% or 99% homologous to the nucleotide sequence as shown in SEQ ID NO: 7, and encodes a protein having the phytase activity.

5. The signal peptide for enhancing the secretory expression of *Escherichia coli* phytase in a filamentous fungus according to claim 1, wherein the *Escherichia coli* phytase is encoded by the nucleotide sequence as shown in SEQ ID NO: 8; or a nucleotide sequence that is at least 95%, 96%, 97%, 98% or 99% homologous to the nucleotide sequence as shown in SEQ ID NO: 8, and encodes a protein having the phytase activity.

6. The signal peptide for enhancing the secretory expression of *Escherichia coli* phytase in a filamentous fungus according to claim 3, wherein the signal peptide is encoded by the nucleotide sequence as shown in SEQ ID NO: 12.

* * * * *